United States Patent [19]
Sugrue et al.

[11] Patent Number: 5,433,216
[45] Date of Patent: Jul. 18, 1995

[54] INTRA-ABDOMINAL PRESSURE MEASUREMENT APPARATUS AND METHOD

[75] Inventors: Michael Sugrue, Chipping Norton; Michael Buist, Stanwell Park, both of Australia; Charles C. Boyle, III, Framingham, Mass.

[73] Assignee: Mountpelier Investments, S.A., Vaduz, Liechtenstein

[21] Appl. No.: 76,408

[22] Filed: Jun. 14, 1993

[51] Int. Cl.⁶ ............................................. A61B 5/103
[52] U.S. Cl. .................................... 128/778; 128/780
[58] Field of Search ............................. 128/778, 780; 606/191–194; 604/100

[56] References Cited

U.S. PATENT DOCUMENTS

| | | |
|---|---|---|
| 3,043,309 | 7/1952 | McCarthy . |
| 3,339,552 | 9/1967 | Aillon . |
| 3,395,710 | 8/1968 | Stratton et al. . |
| 3,437,088 | 4/1969 | Bielinski . |
| 3,480,003 | 11/1969 | Crites ............................ 128/780 |
| 3,658,053 | 4/1972 | Fergusson et al. . |
| 3,734,094 | 5/1973 | Calinog . |
| 3,794,041 | 2/1974 | Frei et al. . |
| 3,983,879 | 10/1976 | Todd . |
| 4,003,705 | 1/1977 | Buzza et al. . |
| 4,063,561 | 12/1977 | McKenna . |
| 4,120,292 | 10/1978 | LeBlanc, Jr. et al. . |
| 4,173,981 | 11/1979 | Mortensen . |
| 4,176,659 | 12/1979 | Rolfe . |
| 4,187,856 | 2/1980 | Hall et al. ....................... 128/635 |
| 4,214,593 | 7/1980 | Imbruce et al. ................ 128/748 |
| 4,221,567 | 9/1980 | Clark et al. .................... 128/635 |
| 4,223,513 | 11/1980 | Elder et al. .................... 250/343 |
| 4,224,377 | 11/1980 | Grams ............................ 128/742 |
| 4,233,513 | 11/1980 | Elder et al. .................... 250/343 |
| 4,259,960 | 4/1981 | Taylor . |
| 4,265,249 | 5/1981 | Schindler et al. .............. 128/635 |
| 4,273,636 | 6/1981 | Shimada et al. ................ 128/635 |
| 4,304,239 | 12/1981 | Perlia ............................. 128/642 |
| 4,338,174 | 7/1982 | Tamura .......................... 128/635 |

(List continued on next page.)

FOREIGN PATENT DOCUMENTS 8903659 8/1989 WIPO .

OTHER PUBLICATIONS

A. Shafik, Straining Urethral Reflex, Acta Anat, 1991; 140: 104–107.

B. Buchler, et al., Effects of Pleural Pressure and Abdominal Pressure on Diaphragmatic Blood Flow. Amer Phys Society, 1985.

(List continued on next page.)

*Primary Examiner*—Max Hindenburg
*Attorney, Agent, or Firm*—Harness Dickey & Pierce

[57] ABSTRACT

An improved tonometric catheter can be configured to have one or more pressure transmitting chambers for sensing the internal pressure such as the internal abdominal pressure of a subject. The tonometric catheter is inserted into the patient such as a nasogastric catheter. The pressure sensing chamber in the form of a balloon is insufflated with a pressure transmitting medium when the balloon is in the desired location. After insufflation of the chamber the catheter is connected to a pressure transducer or manometer which then provides an output reading the internal pressure of the subject. The tonometric catheter with a pressure sensing chamber is useful for sensing the internal abdominal pressure such as during laparoscopic surgery. The sensing of internal pressure can also be used at other locations along the gut or in the cranium. The monitoring of internal pressure is also useful in conjunction with the monitoring of internal pH. The monitored internal pressure can be used to calculate a correction factor which is in turn applied to the calculation of pHi from the measured concentration of gases inside the subject. The pressure sensing chamber can also be used as a location device to ensure the proper location of the chamber and hence the related apparatus on a catheter.

39 Claims, 16 Drawing Sheets

U.S. PATENT DOCUMENTS

| | | | |
|---|---|---|---|
| 4,368,737 | 1/1983 | Ash | 604/283 |
| 4,381,011 | 4/1983 | Somers, 3rd. | 128/635 |
| 4,384,586 | 5/1983 | Christiansen | 128/635 |
| 4,423,739 | 1/1984 | Passaro et al. | 128/719 |
| 4,432,366 | 2/1984 | Margules | 128/635 |
| 4,480,190 | 10/1984 | Burough et al. | 250/343 |
| 4,497,324 | 2/1985 | Sullivan et al. | 128/736 |
| 4,516,580 | 5/1985 | Polanyi | 128/632 |
| 4,534,825 | 8/1985 | Koning et al. | 156/644 |
| 4,576,590 | 3/1986 | Fiddian-Green | 604/26 |
| 4,580,560 | 4/1986 | Straith | . |
| 4,583,969 | 4/1986 | Mortensen | 604/49 |
| 4,596,931 | 6/1986 | Ehnholm et al. | 250/343 |
| 4,610,656 | 9/1986 | Mortensen | 604/4 |
| 4,643,192 | 2/1987 | Fiddian-Green | 128/632 |
| 4,671,287 | 6/1987 | Fiddian-Green | 128/631 |
| 4,727,730 | 3/1988 | Boiarski et al. | 128/667 |
| 4,738,668 | 4/1988 | Bellotti et al. | 604/283 |
| 4,774,956 | 10/1988 | Kruse et al. | 128/635 |
| 4,784,660 | 11/1988 | Fischell | 623/14 |
| 4,790,328 | 12/1988 | Young | 128/748 |
| 4,792,330 | 12/1988 | Lazarus et al. | 604/174 |
| 4,809,710 | 3/1989 | Williamson | 128/780 |
| 4,850,958 | 7/1989 | Berry et al. | 604/26 |
| 4,859,858 | 8/1989 | Knodle et al. | 250/504 R |
| 4,859,859 | 8/1989 | Knodle et al. | 250/504 R |
| 4,873,990 | 10/1990 | Holmes et al. | 128/778 |
| 4,907,166 | 3/1990 | Corenman et al. | 364/497 |
| 4,914,720 | 4/1990 | Knodle et al. | 250/343 |
| 4,966,578 | 10/1990 | Baier et al. | 604/26 |
| 4,981,470 | 1/1991 | Bombeck | 128/780 |
| 4,998,527 | 3/1991 | Meyer | 128/6 |
| 5,002,055 | 3/1991 | Merki et al. | 128/635 |
| 5,042,522 | 8/1991 | Corenman et al. | 137/239 |
| 5,067,492 | 11/1991 | Yelderman et al. | 128/719 |
| 5,095,913 | 3/1992 | Yelderman et al. | 128/719 |
| 5,095,913 | 3/1992 | Yelderman et al. | 128/719 |
| 5,158,083 | 10/1992 | Sacristan et al. | 128/635 |
| 5,167,237 | 12/1992 | Rabin et al. | 128/748 |
| 5,174,290 | 12/1992 | Fiddian-Green | 128/632 |
| 5,186,172 | 2/1993 | Fiddian-Green | 128/632 |

OTHER PUBLICATIONS

John Henry Shenasky II, M.D. et al., The Renal Hemodynamic and Functional Effects of External Counterpressure., Surgery, Gynecology & Obstetrics, Feb. 1972, vol. 134.

D. M. Hargreaves. Raised Intra-abdominal Pressure and Renal Failure, Anaesthesia 1991; 46: 326-7.

J. Ali, M.D., FRCS(C), FACS, and W. Qi, MSc. The Cardiorespiratory Effects of Increased Intra-Abdominal Pressure in Diaphragmatic Rupture. Jour of Trauma, vol. 33, No. 2, 1992.

J. Ducas, M.D., et al. Thoracicoabdominal Mechanics During Resuscitation Maneuvers. Chest, 84/4, Oct 1983.

Fanti J. Andrew, MD, et al., Efficacy of Bladder Training in Older Women With Urinary Incontinence. JAMA, Feb 6, 1991—vol. 265, No. 5.

Shafik, Ahmed, et al., Dynamic Study of Rectal Detrusor Activity at Defecation, Digestion 1991;49:167-174.

Lawrence N. Dibel, M.D., et al., Effect of Increased Intra-Abdominal Pressure on Mesenteric Arterial and Intestinal Mucosal Blood Flow, Journal of Trauma, vol. 22, No. 1, 1992.

Lacey, J. Bruce, et al., The Relative Merits of Various Methods of Indirect Measurement of Intra-abdominal Pressure as a Guide to Closure of Abdominal Wall Defects, Journal Pediatic Surg, vol. 22, No. 12 1987.

Bagley, Nancy A., et al., Urodynamic Evaluation of Voluntary Detrusor Response in Healthy Subjects, Arch Phys Med Rehabil. vol. 66, Mar. 1985.

Cresswell, A. G., et al., Observations on Intra-abdominal Pressure and Patterns of Abdominal Intra-muscular Activity in Man, Acta Physiol Scand 1992, 144, 409–418.

Ali, J. et al., "The Cardiorespiratory Effects of Increased Intra-Abdominal Pressure in Diaphragmatic Rupture," J. Trauma 33:233-239 (1992).

(List continued on next page.)

OTHER PUBLICATIONS

Anzivino, M. J. et al., "Elevated Systemic to Intramucosal Stomach Wall pH–GAP in Patients with Sepsis," *Chest* 98(2) (1990) Suppl.

Badgwell, J. M. et al., "End–Tidal Carbon Dioxide Pressure in Neonates and Infants Measured by Aspiration and Flow–Through Capnography," *J. Clin. Monit.* 7:285–288 (1991).

Bagley, N. A. et al., "Urodynamic Evaluation of Voluntary Detrusor Response in Healthy Subjects," *Arch. Phys. Med. Rehabil.* 66:160–163 (1985).

Barnes, G. E. et al., "Cardiovascular Responses to Elevation of Intra–Abdominal Hydrostatic Pressure," *Am. J. Physiol.* 48:R208–R213 (1985).

Bass, B. L., et al., "Intraluminal $pCO_2$: A reliable indicator of Intestinal Ischemia," *J. Surg. Res.* 39:351–360 (1985).

Bergofsky, E. A., "Determination of Tissue $O_2$ Tensions by Hollow Visceral Tonometers: Effect of Breathing in Enriched $O_2$ Mixtures" *J. Clin. Invest.* J. Clin. Invest. 43:193–200 (1964).

Boda, D. et al., "Gastrotonometry an Aid to the Control of Ventilation During Artificial Respiration," *Lancet* Jan. 24, 1959 pp. 181 and 182.

Bradley, S. E. et al., "The Effect of Increased Intra–Abdominal Pressure on Renal Function in Man," *J. Clin. Invest.* 26:1010–1022 (1947).

Brantigan, J. W. et al., "A Teflon Membrane for Measurement of Blood and Intramyocardial Gas Tensions by Mass Spectroscopy," *J. Applied Physiol.* 32:276–282 (1972).

Bryant, T. N. et al., "Indirect Monitoring and Analysis of Truncal Stress Over Extended Time Periods," *J. Biomed. Eng.* 8:172–174 (1986).

Buchler, B. et al., "Effects of Pleural Pressure and Abdominal Pressure on Diaphragmatic Blood Flow," *J. Applied Physiol.* 58:691–697 (1985).

Burchard, K. W. et al., "Positive and Expiratory Pressure with Increased Intra–Abdominal Pressure," SGO 161:313–318 (1984).

Cadwell, C. B. et al., "Evaluation of Intra–Abdominal Pressure and Renal Hemodynamics," *Current Surg.* 43:495–498 (1986).

Cadwell, C. B. et al., "Changes in Visceral Bllod Flow with Elevated Intraabdominal Pressure," *J. Surg. Res.* 43:14–20 (1987).

Celoria, G. et al., "Oliguria from High Intra–Abdominal Pressure Secondary to Ovarian Mass," *Crit. Care Med.* 15:78–79 (1987).

Cerabona, T. et al., "Urinary Bladder Measurements of Intra–Abdominal Pressure (IAP) in Ascitic Cirrhotics Predictive of Hemodynamic and Renal Function," *Crit. Care Med.* 16:431 (1988).

Collee, G. G. et al., "Bedside Measurement of Intra–Abdominal Pressure (IAP) Via an Indwelling Naso–Gastric Tube: Clinical Validation of the Technique," *Intensive Care Med.* 19:478–480 (1993).

Cresswell, A. G. et al., "Observations on Intra–Abdominal Pressure and Patterns of Abdominal Intra–Muscular Activity in Man," *Acta. Physiol. Scand.* 144:409–418 (1992).

Cresswell, A. G.; et al., "Intra–Abdominal Pressure and Patterns of Abdominal Muscle Activation in Isometric Trunk Flexion and Extension," *Abstracts—International Society of Biomechanics XII Congress* p. 998 (1989).

Cullen, D. J. et al., "Cardiovascular, Pulmonary, and Renal Effects of Massively Increased Intra–Abdominal Pressure in Critically Ill Patients," *Crit. Care Med.* 17:118–121 (1989).

Daly, R. C. et al., "Abdominal Reexploration for Increased Intra–Abdominal Pressure and Acute Oliguric Renal Failure," *Contemp. Surg.* 35:11–18 (1989).

Dawson, A. M., "Small Bowel Tonometry: Assessment of Small Mucosal Oxygen Tension in Dog and Man," *Nature* 206:943–944 (1965).

Diebel, L. N. et al., "Effect of Increased Intra–Abdominal Pressure on Mesenteric Arterial and Intestinal Mucosal Blood Flow," *J. Trauma* 33(1):45–49 (1992).

Diebel, L. et al., "Effect of Intra–Abdominal Pressure on Abdominal Wall Blood Flow," *Am. Surg.* 58:573–576 (1992).

Diebel, L. N. et al., "Effect on Increased Intra–Abdominal Pressure on Hepatic Arterial, Portal Venous, and Hepatic Microcirculatory Blood Flow," *J. Trauma* 33:279–283 (1992).

Ducas, J. et al., "Thoracicoabdominal Mechanics During Resuscitation Maneuvers," *Chest* 84/4 (1983).

Elder, J. B. et al., "Intragastric $PCO_2$ in Man and Calculated Gastric Bicarbonate Concentrations: Effect of Carbenoxolone Sodium," *Carbenoxolone Effect on Intragastric $PCO_2$ and $HCO_3$* pp. 19–25 (1980).

(List continued on next page.)

OTHER PUBLICATIONS

Emerson, H., "Intra-Abdominal Pressures," *Arch. Int. Med.* 7:754–784 (1911).

Fairbank, J. C. et al., "Intraabdominal Pressure Rise During Weight Lifting as an Objective Measure of Low-Back Pain," *Spine* 5(2):179–184 (1980).

Fantl, J. et al., "Efficacy of Bladder Training in Older Women with Urinary Incontinence," *JAMA* 265(5):609–613 (1991).

Fiddian-Green presentation "Advances in ICU Monitoring Techniques," Oct. 25–29, 1992.

Fiddian-Green, R. G., "pH-Gap: A Measurement for Estimating the Presence or Absence of Intestinal Mucosal Ischemia Independently of Disturbances in Systemic Acid Base Balance," (Abstract) ESSR Meeting in Finland (May 23–26, 1993).

Fiddian-Green, R. G., "Should Measurement of Tissue pH and $PO_2$ be Included in the Routine Monitoring of Intensive Care Unit Patients?" *Crit. Care Med.* 19:141–143 (1991).

Fietsam, R. et al., "Intra-Abdominal Compartment Syndrome as a Complication of Ruptured Abdominal Aortic Aneurysm Repair", *Am. Surg.* 55:396–402 (1989).

Fischer, M., "Raised Intra-Abdominal Pressure, Renal Failure and the Bumble Bee", *Int. Care Med.* 16:285–286 (1990).

Guazzi, M. et al., "Negative Influences of Ascites on the Cardiac Function of Cirrhotic Patients," *Am. J. Med.* 59:165–170 (1975).

Gutierez, G. et al., "Gastric Intramucosal pH as a Therapeutic Index of Tissue Oxygenation in Critically Ill Patients" *The Lancet* 339:195–199 (1992).

Guyton, A. C. et al., "Quantiative Aspects of the Collapse Factor in Relation to Venous Return," *Am. J. Physiol.* 177:523–527 (1954).

Hamilton, J. D. et al., "Observations upon Small Gut Mucosal $pO_2$ and $pCO_2$ in Anesthetized Dogs," *Gastroenterology* 55:52–60 (1968).

Hargreaves, D. M., "Raised Intra-Abdominal Pressure and Renal Failure," *Anaesthesia* 46:796 (1991).

Harman, K. P. et al., "Elevated Intra-Abdominal Pressure and Renal Function," *Ann. Sur.* 196:594–597 (1982).

Higgins, J. R. et al., "Tension Pneumoperitoneum: A Surgical Emergency," *Br. J. Hos. Med.* pp. 160–161 (1988).

Hoffman, R. A. et al., "End-Tidal Carbon Dioxide in Critically Ill Patients during Changes in Mechanical Ventilation," *Am. Ref. Respir. Dis.* 140:1265–1268 (1989).

Hunt, T. K. "A New Method of Determining Tissue Oxygen Tension," *Lancet* 1370–1371 (1964).

Iberti, T. J. et al., "Determination of Intra-Abdominal Pressure Using a Transurethral Bladder Catheter: Clinical Validation of the Technique," *Anesthersiology* 70:47–50 (1989).

Jacques, T., et al., "Improvement of Renal Function after Relief of Raised Intra-Abdominal Pressure due to Traumatic Retroperitoneal Haematoma," *Anasth. Intens. Care.* 16:478–494 (1988).

Jellinek, H. et al., "Arterial to End-Tidal $CO_2$ Tension Difference After Bilateral Lung Transplantation," *Crit. Care Med.* 21(7):1035–1040 (1993).

Kaback, K. et al. "Letters JAMA" *JAMA* 254:1035 (1985).

Kashtan, J. et al., "Haemodynamic Effects of Increased Abdominal Pressure," *J. Surg. Res.* 30:249–255 (1981).

Kelly, K. et al., "A Simple Non-Invasive Technique to Measure Intra-Abdominal Pressure," *Crit. Care* p. 366 (1987).

Kelly, K. M. et al. "A Simple Non-Invasive Technique to Measure Intra-Abdominal Pressure," (Abstracts) p. 371 1989.

Kivilaakso, E., et al. "Gastric Blood Flow, Tissue Gas Tension and Microvascular Changes During Hemorrhage-Induced Stress Ulceration in the Pig," *Am. J. Surg.* 143:322–330 (1982).

Kivisaari, J. et al., "Use of Silastic Tube and Capillary Sampling Technic in the Measurement of Tissue $PO_2$ and $PCO_2$," *Am. J. Surg.* 125:623–627 (1973).

Kram, H. B. et al., "Noninvasive Measurement of Tissue Carbon Dioxide Tension Using a Fiberoptic Conjunctival Sensor: Effects of Respiratory and Metabolic Alkalosis and Acidosis," *Crit. Care Med.* 16:280–284 (1988).

Kron, I. L. et al., "The Measurement of Intra-Abdominal Pressure as a Criterion for Abdominal Re-Exploration," *Ann. Surg.* 199:28–30 (1984).

Lacey, S. R., et al., "The Relative Merits of Various Methods of Indirect Measurement of Intraabdominal Pressure as a Guide to Closure of Abdominal Wall Defects," *J. Ped. Surg.* 22(12):1207–1211 (1987).

Landers, B. R. et al., "Response of Porcine Lower Esophageal Sphincter to Increasing Intraabdominal Pressure," *Dig. Dis. Sci.* 32:272–279 (1987).

(List continued on next page.)

OTHER PUBLICATIONS

Lawson, D. et al., "Stability and Long-Term Durability of Raman Spectroscopy," *J. Clin. Monit.* 9:241–151 (1993).

Lenz, G. et al., "Capnometry for Continuous Postoperative Monitoring of Nonintubated, Spontaneously Breathing Patients," *J. Clin. Monit.* 7:245–248 (1991).

Leon, A. et al., "Septic Shock: Does Gastric Mucosal Tonometry Assess Tissue Oxygenation?" 79(3A) (1993).

Le Roith, D. et al., "The Effect of Abdominal Pressure on Plasma Antidiuretic Hormone in the Dog," *J. Sur. Res.* 32:65–69 (1982).

Luiz, T. et al. "Veranderungen der Ventilation Wahrend Laparoskopischer Cholezystektomie," *Anaestheisist* 41:520–529 (1992).

Martinez-Pellus, A. E. et al., "Can Selective Digestive Decontamination Avoid the Endotoxemia and Cytokine Activation Promoted by Cardiopulmonary Bypass?" *Crit. Care Med.* 21:1684–1691 (1993).

McCarthy, T. A., "Validity of Rectal Pressure Measurements as Indication of Intra-Abdominal Pressure Changes During Urodynamic Evaluation," *Urology* 6:657–660 (1982).

McGee, Lemuel et al., "The Carbon Dioxide Tension and Acid-Base Balance of Jejunal Secretions in Man," 893–904 (1941).

McIver, M. A. et al., "Gaseous Exchange Between the Blood and the Lumen of the Stomach and Intestines," *Am. J.Physiol.* 76(1):92–111 (1926).

Motew, M. et al., "Cardiovascular Effects and Acid–Base and Blood Gas Changes during Laparoscopy," *Am. J. Obstet, Gynecol.* 115:1002–1012 (1972).

Niemczyk, T. M. et al., "Multichannel Raman Spectroscopy Tackles Industrial Problems," *Laser Focus World* Mar.: 85, 86, 88, 90, 92, 95, 97 and 98 (1993).

Noc, M. et al., "Comparison of Gastric Luminal and Gastric Wall $PCO_2$ During Hemorrhagic Shock," *Cir. Shock* 40:194–199 (1993).

Nordin, M. et al. "Intra-Abdominal Pressure Measurements Using a Wireless Radio Pressure Pill and Two Wire Connected Pressure Transducers: A Comparison," *Scand. J. Rehab. Med.* 16:139–146 (1984).

O'Leary M. J. et al., "Acute Renal Failure in Association with Pneumatic Antishock Garment and with Tense Ascites," *Anesthesia* 46:326–327 (1991).

Overholt, R. H., "Intraperitoneal Pressure," *Arch. Surg.* 22(5):691–703 (1931).

Paulus, D. A., "Capnography," *Int'l. Anes. Clin.* 27(3):167–174 (1989).

Platell, C. F. et al., "Impaired Renal Function Due to Raised Intraabdominal Pressure," *Intensive Care Med.* 16:328–329 (1990).

Raemer, D. B. et al., "Variation in $PCO_2$ between Arterial Blood and Peak Expired Gas during Anesthesia," *Anest. Analg.* 62:1065–1069 (1983).

Raemer, D. B. et al., "Accuracy of End-Tidal Carbon Dioxide Tension Analyzers," *J. Clin. Monit.* 7(2):195–208 (1991).

Richards, W. O. et al., "Acute Renal Failure Associated with Increased Intra-Abdominal Pressure," *Ann. Surg.* 197:183–187 (1983).

Ring, J. C. et al., "Effects of Acute Tense Abdominal Distension on Regional Blood Flow and Renal Function," *Critical Care Med.* 12:222 (1984).

Rodrigues, A. A. et al., "Therapeutic Exercise in Chronic Neck and Back Pain," *Arch. Phys. Med. Rehab.* 73:870–875 (1992).

Rowen, D. et al., "An Investigation of Bladder-Urethral Function by Pressure-Flow Studies," *BioMed Eng.* 304–308 (1972).

Roy, J. et al., "An Improved Nasal Prong Apparatus for End-Tidal Carbon Dioxide Monitoring in Awake, Sedated Patients," *J. Clin. Monit.* 7(3):249–252 (1991).

Rune, S. J. et al., "Carbon Dioxide Tensions in the Proximal Part of the Canine Gastrointestinal Tract," *Gastroenterology* 56:758–762 (1969).

Rune, S. J., "Acid-Base Parameters of Duodenal Contents in Man," *Gastroenterology* 62:533–539 (1972).

Salzman, A. L. et al. "Air Tonometry: A New Method for Determination of Gastrointestinal Mucosal $PCO_2$," *Crit. Care Med.* 21(4):S202 (1993).

Savino, J. A. et al., "Manipulation of Ascitic Fluid Pressure in Cirrhotics to Optimize Hemodynamic and Renal Function," *Ann. Surg.* 208:504–511 (1988).

Scannell, G. et al., "Tissue Oximetry in Hemorrhagic Shock and Resuscitation: Gastric But not Rectal Submucosal $pO_2$ Correlates with Gut Translocation," *Crit. Care Med.* 22:A187 (1993) (abstract).

Severinghaus, J. W. et al., "Correction Factors for Infrared Carbon Dioxide Pressure Broadening by Nitrogen, Nitrous Oxide and Cyclopropane," *Anesthesiology* 22(3):429–432 (1961).

Shafik, A. et al., "Dynamic Study of Rectal Detrusor Activity at Defecation," *Digestion* 49:167–174 (1991).

Shafik, A., "Straining Urethral Reflex: Description of a Reflex and its Clinical Significance," *Acta Nat.* 140:104–107 (1991).

Shafik, A., "Esophago-Rectal Reflex: Description and
(List continued on next page.)

OTHER PUBLICATIONS

Clinical Significance," *Int. Surg.* 78:83–85 (1993).

Shafik, A., "Straining Puborectalis Reflex: Description and Significance of a 'New' Reflex," *Anatomical Record* 229:281–284 (1991).

Shelly, M. P. et al., "Haemodynamic Effects Following Surgical Release of Increased Intra-Abdominal Pressure," *Br. J. Anaesth.* 59:800–805 (1987).

Shenasky, J. H. et al. "The Renal Haemodynamic and Functional Effects of External Counterpressure," *Surg. Gynecol. Obstet.* 134:253–258 (1972).

Siesjo, B. K., "A Method for Continuous Measurement of the Carbon Dioxide Tension on the Cerebral Cortex," *Acta Physiol. Scand.* 51:297–313 (1961).

Sloan, S. et al., "Determinants of Gastroesophageal Junction Incompetence: Hiatal Hernia, Lower Esophageal Sphincter, or Both?," *Am. College of Phys.* 117:977–982 (1992).

Smith, J. H. et al., "Reversal of Post-Operative Anuria by Decompressive Celiotomy," *Arch. Int. Med.* 145:553–554 (1985).

Smith-Wright, D. L. et al. "The Hemodynamic Effects of Dopamine and/or Volume Expansion in Acute Tense Abdominal Distension," *Crit. Care Med.* 270 (1985).

Starlinger, M. et al., "H+ Back Diffusion Stimulating Gastric Mucosal Blood Flow in the Rabbit Fundus," *Surgery* 89:232–236 (1981).

Stock, M. C., "Noninvasive Carbon Dixoide Monitoring: Capnography," *Crit. Care Clin.* 4(3):511–526 (1988).

Stone, H. H. et al., "Renal Decapsulation in the Prevention of Post-Ischemic Oliguria," *Ann. Surg.* 186:343–355 (1977).

Sussman, A. M. et al., "Effect of Positive End-Expiratory Pressure on Intra-Abdominal Pressure," *South Med. J.* 84:697–700 (1991).

Thompson, D. G., et al., "Normal Patterns of Human Upper Small Bowel Motor Activity Recorded by Prolonged Radiotelemetry," *GUT* 21:500–506 (1980).

van Gool, J. D. et al., "Measurement of Intravesical and Rectal Pressures Simultaneously with Electromyography of Anal. Sphincter in Children with Myelomeningocele," *Develop. Med. Child Neurol.* 18:287–301 (1976).

Vurek, G. G. et al., "A Fiber Optic $PCO_2$ Sensor," *Annal. Biomed. Eng.* 2:499–510 (1993).

Walton, D. M. "Continuous Monitoring of Blood pH, $PCO_2$ and $PO_2$ in Clinical Practice," Fifth ISA Biomedical Sciences Instrumentations Supposium, Denver, Colo., May 1970 pp. 155–158.

Westenskow, D. R. et al., "Clinical Evaluation of a Raman Scattering-Multiple Gas Analyzer for the Operating Room," *Anesthesiology* 70:350–355 (1989).

Westenskow, D. R. et al., "Raman Scattering for Respiratory Gas Monitoring in the Operating Room: Advantages, Specifications, and Future Advances," *Biomed. Instru. Tech.* Nov./Dec.: 485–489 (1989).

Westenskow, D. R. et al. "Can the Raman Scattering Analyzer Compete with Mass Spectrometers: An Affirmative Reply," *J. Clin. Monit.* 5(1):34–36 (1989).

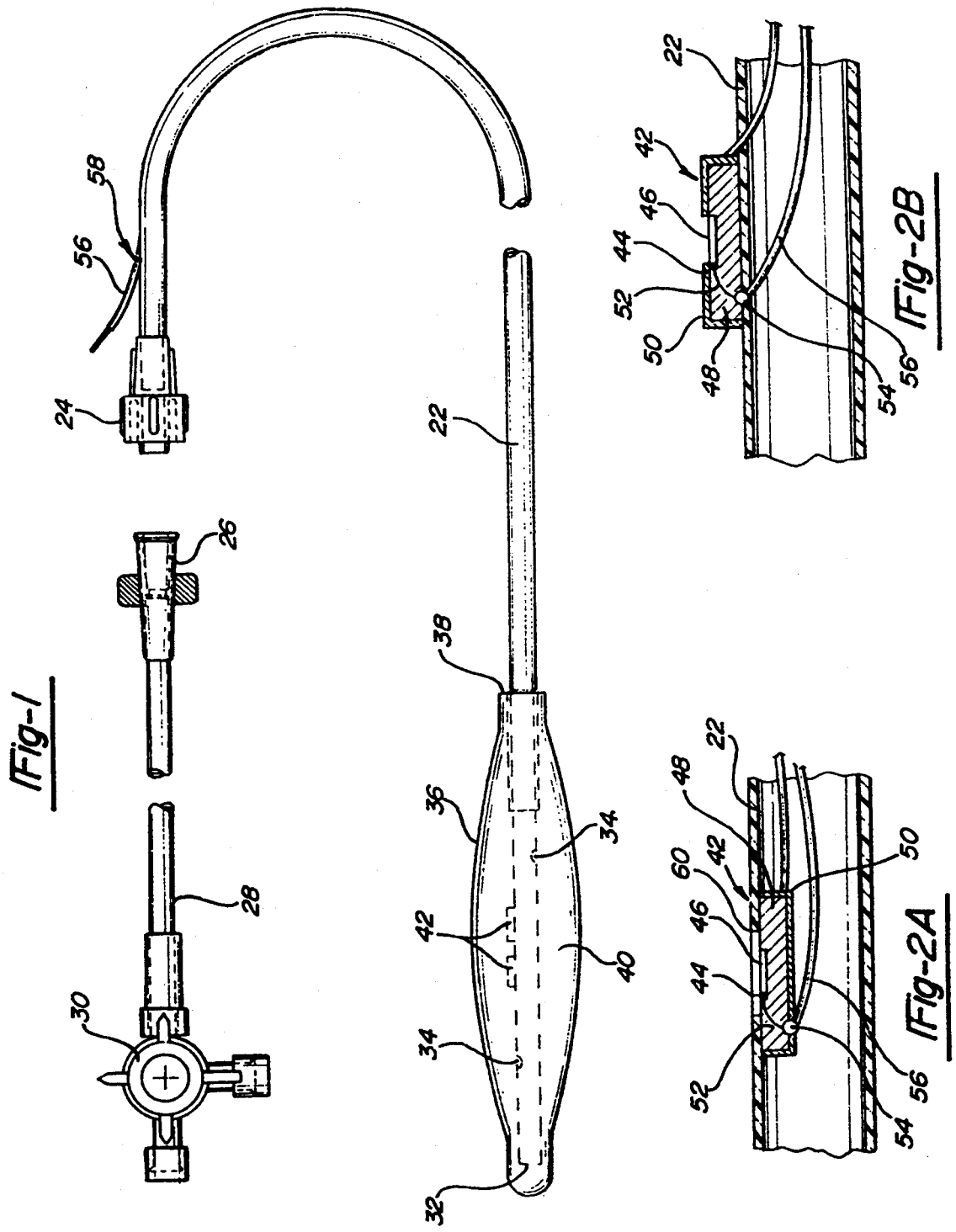

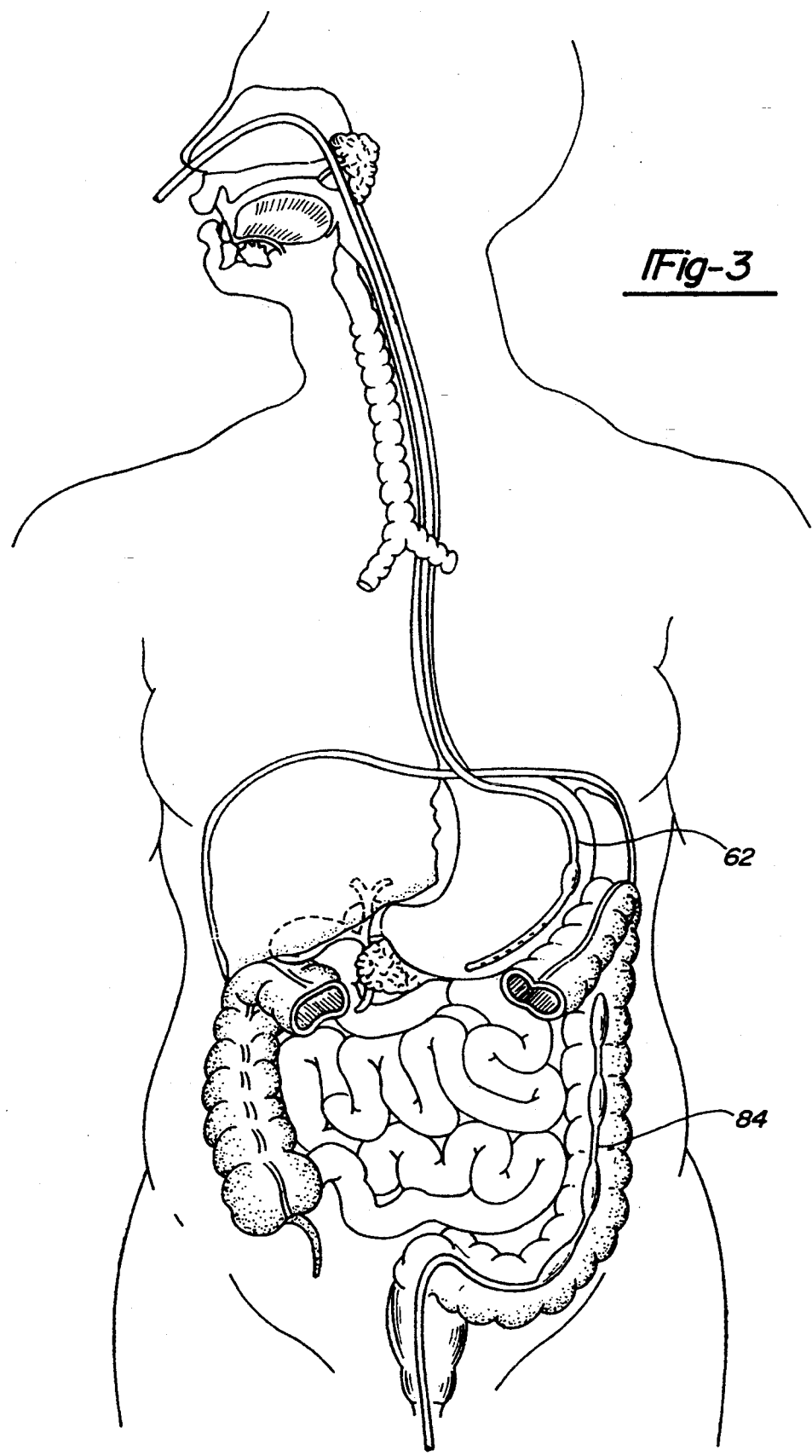

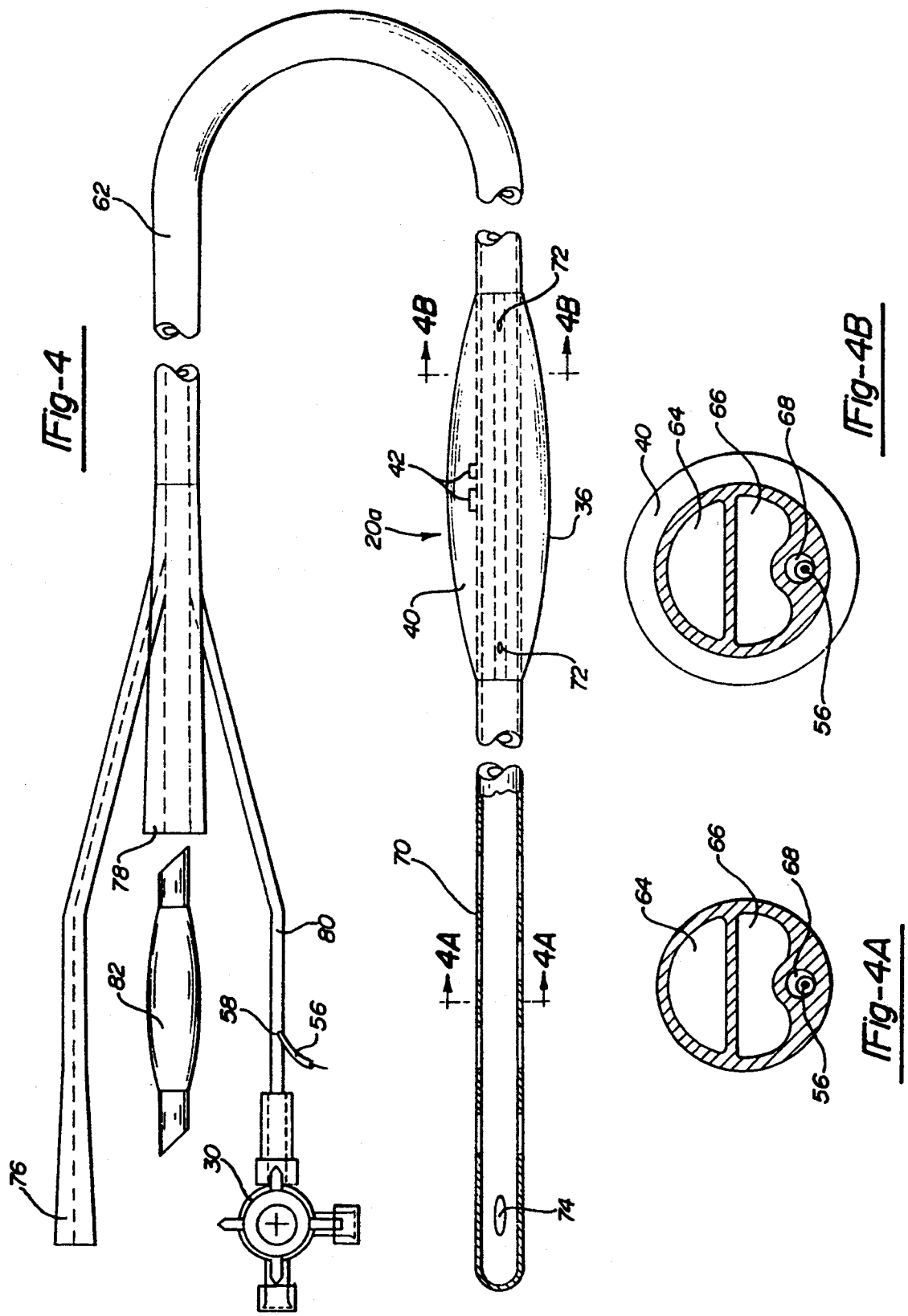

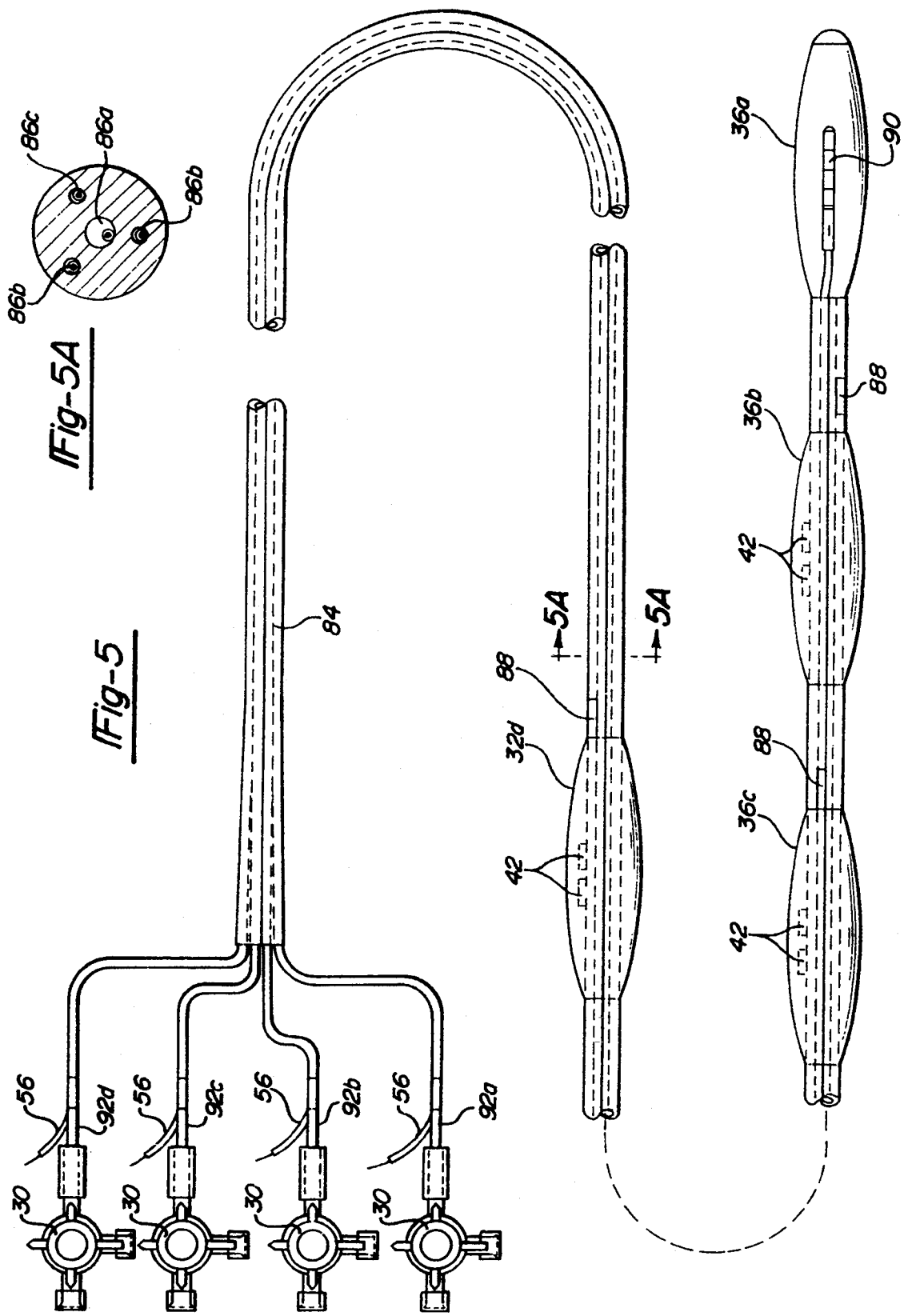

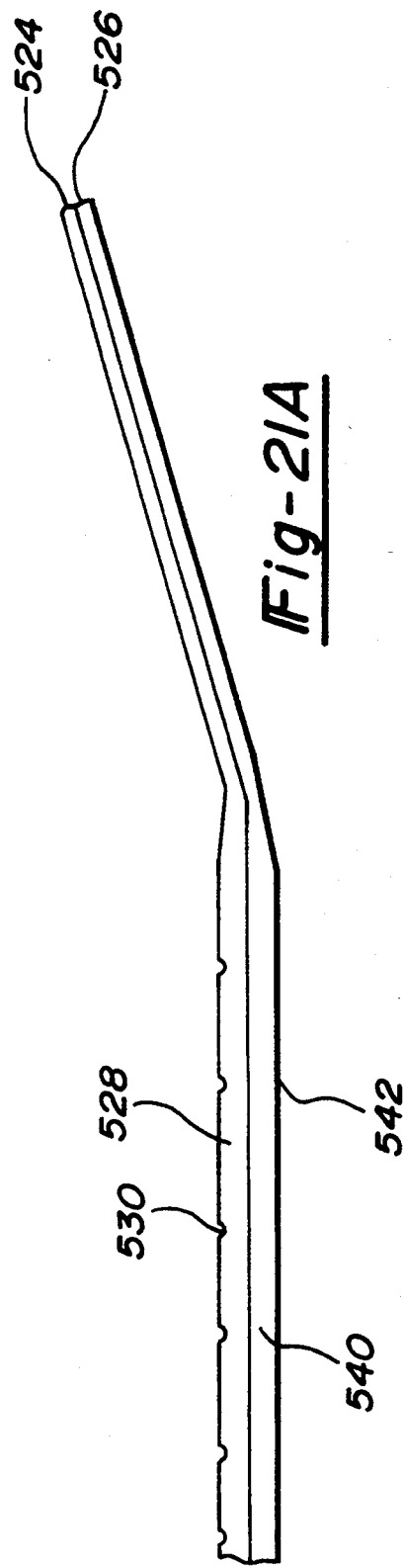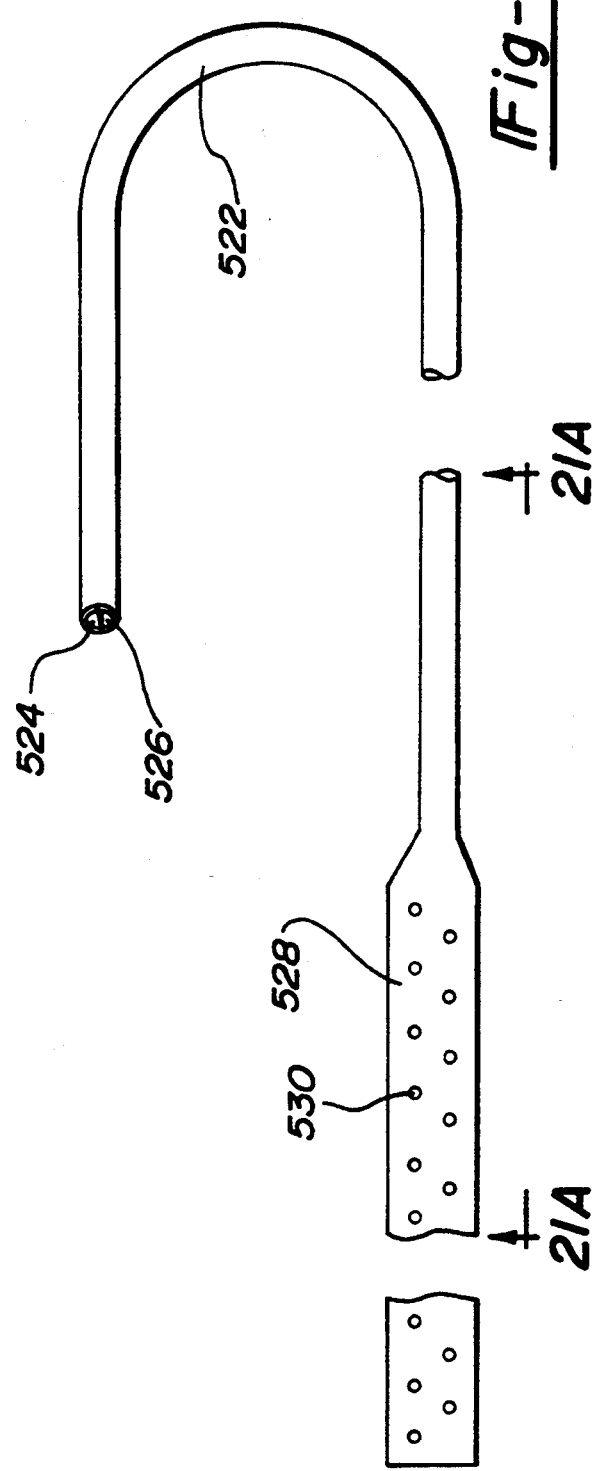

INTRA-ABDOMINAL PRESSURE MEASUREMENT APPARATUS AND METHOD

BACKGROUND AND SUMMARY OF THE INVENTION

This invention relates to medical diagnostic equipment and methods and is particularly concerned with hollow viscus tonometry and direct or remote sensing of pressure within organs such as intra-abdominal pressure (IAP) and related properties indicative of the condition of the internal organs.

Until the advent of the tonometric method (see U.S. Pat. No. 4,643,192, issued Feb. 17, 1987) few considered any aspect of acid-base balance when attempting to monitor or maintain the adequacy of tissue oxygenation. Yet acid-base balance is primarily determined by the balance between the protons released during the release of energy by ATP hydrolysis and the resynthesis of ATP by oxidative phosphorylation. The hydrolysis of ATP generates 150,000 mmols of H+ each day in a resting 70 Kg man. All, but the 1% of this fixed acid load excreted by the kidneys each day, is presumed to be consumed in the resynthesis of ATP by oxidative phosphorylation. When the delivery of oxygen fails to satisfy the energy needs of the tissue the rate of ATP hydrolysis exceeds the rate of synthesis and the pH falls as the degree of unreversed ATP hydrolysis increases.

It is now widely accepted that global measurements of oxygen delivery, consumption and extraction do not provide reliable information about the adequacy of local or even "global" tissue oxygenation in patients. The indirect measurement of gastric intramucosal pH (pHi) as described in U.S. Pat. Nos. 4,643,192; 5,158,083; 5,186,172 provides clinicians with a minimally invasive yet sensitive means of detecting the development of a tissue acidosis, and hence inadequacy of tissue oxygenation, in a region of the body that is one of the first to exhibit an inadequacy of tissue oxygenation in shock. Use of the measurement has revealed that some 50% to 60% of patients having major surgery and 80% of ICU patients develop an intramucosal acidosis during their illness despite the conventional appearance of being adequately resuscitated.

The degree and duration of the presence of a gastric intramucosal acidosis are highly sensitive measures of the risk of developing ischemic gut mucosal injury and its putative consequences, namely the translocation of bacteria and their toxins, cytokine release, organ dysfunctions and failures, and death from the organ failures. By providing an index of the adequacy of tissue oxygenation in one of the first parts of the body to exhibit dysoxia in shock the measurement of gastric intramucosal pH improves the opportunity to obtain advanced and accurate warning of impending complications and to intervene in time to prevent them. More importantly timely therapeutic measures that restore the intramucosal pH to normality and "gut-directed" therapies incorporating measures that reverse an intramucosal acidosis are associated with an improved outcome. "pH-directed" therapy has in addition been shown to improve outcome in a prospective randomized multicenter study of medical and surgical ICU patients.

The measurements of gastric intramucosal pH have revealed deficiencies in currently accepted practices. It has, for example, become apparent that empirical increases in global oxygen delivery may be redundant in some 40% to 50% of patients having major cardiovascular surgery who do not develop a gastric intramucosal acidosis and whose prognosis is excellent. It is further apparent that the vogue of increasing global oxygen delivery to supranormal levels cannot be relied upon to prevent or to reverse the presence of an intramucosal acidosis. Of particular concern is the intramucosal acidosis that may be induced by measures, notably the transfusion of red blood cells and dobutamine, that increase global oxygen delivery in patients who do not have an intramucosal acidosis but whose global oxygen delivery is considered too low.

Intra-abdominal pressure (IAP) measurement is increasingly used in clinical practice as a guide to intraperitoneal pathology and as a predictor of renal function. In particular, IAP monitoring may be useful in the increasing practice of minimally invasive procedures such as laparoscopic surgery. In laparoscopic surgery gas is insufflated into the peritoneum to provide an operating field and improve the field of vision. Steps are taken to monitor the IAP caused by the insufflated gas to reduce the chances of overinsufflation.

Increased IAP may be associated with a variety of clinical situations that may adversely affect cardiac, renal, respiratory, and metabolic functions. See Iberti, et al., *The Determination Of Intra-Abdominal Pressure Using A Transurethral Bladder Catheter: Clinical Validation of the Technique* Anesthesiology, Vol. 70, No. 1, January 1989, p. 47. Diebel, et al., *Effect Of Increased Intra-Abdominal Pressure On Hepatic Arterial, Portal Venous And Hepatic Microcirculatory Blood Flow*, The Journal Of Trauma, Vol. 33, No. 2, 1992, p. 279 and references cited therein which are expressly incorporated by references herein.

Examples of situations where IAP monitoring may be useful include trauma, aneurism repair, laparoscopic surgery, massive edema, and bowel distention. The measurement of IAP may be complimentary to monitoring intramucosal pH as studies have demonstrated an increase in IAP may cause a reduction of blood flow to the microcirculation of the gut thus causing a fall in intramucosal pH.

A number of different techniques have been used to measure IAP. The measurement of IAP was performed in the last century using rectal and oesophageal sounds connected to a Marcy tambour. Wagoner GW, American Journal of Medical Science 1926; 171: 697–707. Intra-abdominal pressure has been measured transrectally in dogs—Thorington JM, Schmidt CP, *A Study of Urinary Output and Blood Pressure Changes Resulting in Experimental Ascites*, Am J Med Sci 1923; 165: 880–890. Also used has been a Miller Abbott tube in the rectum and a Hamilton manometer in the stomach to record pressure—Bradley SE, Bradley GP, *The Effect on Increased Intra-abdominal Pressure on Renal Function in Man*, J Clin Invest 1947; 26:1010–1022. IAP has also been measured through invasive techniques namely via catheters inserted transcutaneously into the peritoneal cavity Diebel, et al., Journal Of Trauma, 1992, p. 280. Direct cannulation of the peritoneal cavity and the injection of air have also been used—Emerson H., *Intraabdominal Pressures*, Arch Int Med 1911;7:754—Overholt RH, *Intraperitoneal Pressure*, Arch Surg 1931;22:691–703.

IAP monitoring techniques have been developed for intravesical methods where the bladder is partially filled with saline and the fluid pressure in the bladder has been monitored as an indicium of IAP. The original technique has undergone some modification by Iberti, et al.—Iberti TJ, Lieber CE, Benjamin E., *Determination of Intra-abdominal Pressure Using a Transurethral Bladder catheter, Clinical Validation of the Technique,* Anesthesiology 1989;70:47–50. The intravesical technique has become an accepted standard for IAP monitoring. While reliable, it is cumbersome to perform and interferes with the estimation of the patient's urinary output readings. Because the urinary tract is essentially sealed by the intravesical technique of IAP monitoring, it is also of limited value for continuous IAP monitoring because urine output cannot be indefinitely obstructed.

THE TONOMETRIC METHOD

References to the tonometrics method, tonometrics and tonometer in this application refers to the use of catheters or like devices as part of a system to measure and monitor internal conditions of a subject, such as phi and/or IAP.

The measurement of pH in the most superficial layer of the mucosa is obtained indirectly by measuring the partial pressure of carbon dioxide ($pCO_2$; $PCO_2$) in the lumen of the gut and the bicarbonate concentration in arterial blood and substituting these two values in the Henderson-Hasselbalch equation or some modification thereof. See "Gastric Intramucosal pH as a Therapeutic Index of Tissue Oxygenation in Critically Ill Patients," *Lancet* 1992; 339; 195–99, incorporated herein by reference. The indirect measurement of the pH of the wall of the organ (pH indirect or pHi) may be employed because it is believed or assumed that the $pCO_2$ in the most superficial layers of the mucosa is in equilibrium with that in the lumenal contents with which it is in contact. It is further based upon the assumption that the bicarbonate concentration in the tissue is the same as that being delivered to it in arterial blood and that the pKa, 6.1, is the same as that in plasma.

At present, measurements of $pCO_2$ in the lumen of the stomach are obtained by infusing saline into the silicone balloon of a gastrointestinal tonometer, allowing the $pCO_2$ in the saline to equilibrate with that in the lumen of the gut; recording the equilibration time; aspirating the saline; measuring the $pCO_2$ in the saline with a blood gas analyzer; using a nomogram to derive the steady-state adjusted $pCO_2$ from the equilibration time and the measured $pCO_2$; and then derive the intramucosal pH from the steady-state adjusted $pCO_2$ obtained and the bicarbonate concentration in a substantially contemporaneous sample of arterial blood. Again, see U.S. Pat. Nos. 4,643,192, issued Feb. 17, 1987; 5,174,290, issued Dec. 29, 1992; and 5,186,172, issued Feb. 16, 1993; as well as copending U.S. applications, Ser. No. 719,097, filed Jun. 20, 1991; Ser. No. 994,721, filed Dec. 22, 1992 and Ser. No. 014,624, filed Feb. 8, 1993; all three issued patents being completely and expressly incorporated herein by reference. The precision of the measurement of gastric intramucosal pH between healthy subjects is excellent, the gastric intramucosal pH in a healthy subject being the same as the pH in his arterial blood.

The prior art (see U.S. Pat. No. 4,643,192) has recognized that intestinal ischemia, and to a lesser degree, stress ulceration, are two problems that plague physicians involved in the management of patients in intensive care units. Intestinal ischemia, in particular, has an insidious onset and may not be detected until days after the intestine has become completely and irreversibly compromised. A delay in the diagnosis of intestinal ischemia may have devastating consequences for a patient. The availability of means for early diagnosis and management of patients with these problems would have immediate applicability in all intensive care units, especially where the procedure can be conveniently conducted with reasonable safety and reliability.

It has been established that a fall in the intramucosal pH may precede the development of intestinal ischemia and stress ulceration. As discussed in U.S. Pat. No. 4,643,192, which is expressly incorporated herein by reference, entitled "Hollow Viscus Tonometry" a fall in intramucosal pH also occurs within minutes of inducing intestinal ischemia in dogs. The fall in pH in intestinal mucosa, and hence the likelihood of ischemia or stress ulceration, can be reliably calculated from a $pCO_2$ (partial pressure of $CO_2$), or other indicia of pH, in lumenal fluid and the bicarbonate concentration in arterial blood. The method of calculating the pH in intestinal mucosal tissue, pursuant to principles of the prior U.S. Pat. No. 4,643,192, has been validated by directed measurements under a variety of conditions simulating clinical problems. A correlation coefficient in the order of 0.92 to 0.95 has been obtained in each of 16 dogs. The validity of the procedure is inherently extensible to humans, and indeed may also be useful in assessing the vitality of other hollow organs and tissue. See R. G. Fiddian-Green et al. "Splanchnic Ischemia and Multiple Organ Failure".

To measure the $pCO_2$ in the lumen of the gut it has heretofore been necessary to obtain and remove a sample of fluid that has been in contact with the wall of the gut for a certain time period, usually at least half an hour. It has now been observed that it is somewhat difficult to manually aspirate the sampling fluid or medium from a tonometric catheter located in the gut or other internal focus with any consistency. It is much easier to obtain such samples from the stomach, but samples obtained from the stomach frequently contain foreign material that can damage a gas analyzer.

As taught in the prior U.S. Pat. No. 4,643,192, the desired sample or samples can be obtained from the gut using a catheter tube (called a tonometric catheter) having a walled sampling chamber on the tube with the sampling chamber being in sample-specific communication with the hollow interior of the tube. The wall of the sampling chamber comprises a material which is substantially impermeable to liquid yet is highly permeable to gas. One suitable material is polydimethylsiloxane elastomer.

In use the catheter is introduced into a patient to place the sampling chamber at a desired site within the gut. An aspirating liquid or medium is employed to fill the interior of the sampling chamber. The sampling chamber is left in place at the desired sampling site long enough to allow the gases present to diffuse through the wall of the sampling chamber into the aspirating liquid. The time should be long enough for the gases to equilibrate. The liquid impermeable nature of the sample chamber wall material prevents both the aspirating liquid from leaking out of the chamber and also the intrusion of any liquids into the aspirating liquid. After the appropriate or desired amount of placement time has elapsed the aspirating liquid is aspirated along with the gases which have diffused into it. The sample thus obtained is analyzed for gas content, in particular for $pCO_2$. In this way the $pCO_2$ within the lumen of the gut can be reliably measured with the fluid being free from lumenal debris.

In carrying out the diagnostic method taught in my prior patent the $pCO_2$ measurement is utilized in conjunction with a measurement of the bicarbonate ion concentration ($HCO_3^-$) in an arterial blood sample of the patient for determining the pH of the tract wall.

Depending upon the particular condition of a given patient, the catheter may be left in place and samples may be taken at periodic intervals so that pH values may be periodically calculated. The procedure has a high reliability in accurately determining the adequacy of organ tissue oxygenation, and diagnosing intestinal ischemia in its incipient stages. Such determination or detection can be useful in treating the patient so that the potentially devastating consequences resulting from less timely detection may often be avoided.

While the sampling techniques taught in my prior patent have provided highly accurate and reliable results, it has now been observed that there are instances (in the care of the critically ill in intensive care units, for example) in which remote sensing of the organ or organ-wall condition and automatic determination or calculation of the organ or organ-wall pH would be advantageous and easier to effectuate. This method would thus partially or totally eliminate the need for the somewhat cumbersome aspiration of the sampling fluid or medium which fills the sampling chamber; it may also eliminate the need for the sampling chamber to be in sampling-medium communication with any other part of the device. There is also a need to extend the benefits of tonometric sampling and sensing to other internal hollow viscous organs. To this end, there is a need for new and different tonometric devices specifically adapted to allow my sensing and sampling techniques to be performed with ease in a clinical environment, and in combination with other procedures.

The importance and significance of determining the pH of the wall of a given hollow viscous organ has been recently dramatically magnified as a result of the recent recognition that the pH of the wall of a given organ can be employed to accurately evaluate the vitality and/or stability of that organ as well as others; this is in contrast to merely determining whether such an organ is experiencing an ischemic event. Further, certain organs can be selected for monitoring, either alone or in combination, and evaluation of this organ or these organs can aid in predicting the overall condition of the patient, or the onset of a multitude of pathologies, including predicting or identifying such events as multiple organ failure. Such a methodology can be employed to greatly enhance and supplement the monitoring of the critically ill, for example.

It has also been observed that an unusually large negative bias is encountered when measuring the $pCO_2$ in saline with certain blood gas analyzers (including those manufactured by Nova Biomedical, L. Eschweiler and Mallinckrodt) that have been standardized for blood but not for saline. The presence or absence of unacceptable bias may be determined by the use of reference samples of tonometered saline. The interinstrumental bias encountered when measuring arterial blood gases and especially $pCO_2$ in saline with different blood gas analyzers requires that each institution derive its own normal values for meaningful use in clinical practice. It is reported that the precision of the measurements made within a static environment may be improved and unacceptable interinstrumental bias eliminated, in whole or in part, by using gelofusine, phosphate-buffered or bicarbonate-buffered saline, or mixtures thereof. Unfortunately the diffusional characteristics are altered and, in the case of the buffered saline, the time constant extended from about 18 to about 48 minutes. The nomograms provided for the determination of steady-state adjusted $pCO_2$ in saline cannot be used for the determination of intramucosal pH with these fluids.

The time constant may be reduced to seconds by using an electrochemical $pCO_2$ sensor directly in the lumen of the gut and measuring the $pCO_2$ in either liquid or gaseous luminal contents, as described herein. Unfortunately, $pCO_2$ sensors are known for their ability to drift and cannot be easily recalibrated in vivo. The bias of a measurement of $pCO_2$ made with a conventional $pCO_2$ sensor is a function of the chemical composition of the gaseous or liquid fluid into which it is immersed and must be separately standardized for measurements made in environments of different chemical composition such as blood and saline, as discussed above. In one set of experiments the bias observed in each of two instruments varied between 1% and 45%, the bias in each of the different solutions being consistent between the blood gas analyzers used. The large and frequent changes in the chemical composition of luminal contents, especially in the stomach, almost certainly cause large and unpredictable changes in bias that render measurements made outside the protective environment of a silicone balloon tonometer prone to unacceptable error. The deposition of luminal contents on the electrode membrane is an additional source of potential error with the use of a naked sensor, i.e., one without a tonometric walled sampling chamber.

In one aspect, the present invention provides a new apparatus and method for remotely sensing organ condition and conveying an electromagnetic signal, e.g. an electrical current or optical signal, to an electronic or optical apparatus located outside the organ under investigation. In one embodiment, a chemically sensitive electronic transducer (or plurality of transducers), such as a field effect transistor, is attached to a tonometric catheter for introduction into the organ along with the tonometric catheter. The first electronic sensor, preferably non-temperature, generates and conveys an electromagnetic signal indicative of some desired aspect of organ condition, e.g., indicative of the $pCO_2$, pH and/or $pO_2$ level of the organ or organ-wall. For example, in one preferred embodiment, mean ambient $pCO_2$, pH and/or $pO_2$ of lumenal fluid or the like is measured or monitored via wire or other suitable electromagnetic energy conveying means to an electronic circuit which interprets the electromagnetic signal and produces a report of the organ condition. The electronic circuit may include an input for receiving a separately determined signal indicative of the blood pH of the patient. Using this $pCO_2$, pH and/or $pO_2$ measurement along with blood (preferably arterial) pH data, the electronic circuit determines the pH of the organ wall under test and thereby provides information for determining the organ's current condition or perhaps predicting the organ's future condition. The electronic circuit may be suitably constructed from analog components, digital components or both.

In another embodiment, a pH, $pCO_2$ or $pO_2$ sensitive colorimetric substance is injected into an area adjacent to the organ, e.g., into the sampling chamber of the tonometric catheter, and an optical sensor is employed to detect color change in order to determine the pH of the wall of that organ. The optical sensor can either be disposed in or on the tonometric catheter for introduction into the area adjacent the organ or it may be disposed outside the organ with fiber optic cable optically coupling the sensor to the tonometric catheter site at which the pH sensitive substance has been injected.

In another aspect the present invention provides a variety of new and different tonometric catheter devices for sensing and/or sampling a fluid or gas property (such as pH, $pO_2$, $pCO_2$, and the like) which is indicative of the condition of an internal organ, in conjunction or combination with a walled catheter tube adapted for delivery or draining fluids, such as nasogastric tubes, urinary catheters, ureteric catheters, intestinal feeding tubes, wound or abdominal drains (suction or regular) and biliary tubes, catheters and stents, with or without remote sensing means for pH, $pCO_2$ and/or $pO_2$.

In still another aspect or embodiment, the device employs two separate walled catheter tubes, one tonometric catheter tube for the measurement of a fluid or gas property, that is in communication with the sampling chamber; and a second walled catheter tube adapted for delivering or draining fluids.

In yet another aspect or embodiment, the device employs a walled sampling chamber in communication with a sensing means, and a second walled catheter tube adapted for delivering or draining fluids.

Optionally, when a non-temperature sensing-means is employed, a second sensing-means may be employed as well.

Although not originally thought to be feasible or efficacious, the present invention in yet another embodiment has also accomplished improved accuracy and speed by the effective infrared sensor measurement of liquid or gaseous fluid parameters or compounds of interest, such as $pO_2$, $pCO_2$, pHi, etc., admixed in a gaseous sampling medium, preferably air. This was previously not believed to be possible due to the high gas volumes typically required for accurate infrared measurements, and because of erroneous measurements resulting from increased gas densities caused by higher tonometric sampling medium pressures.

In view of all of the above, it will be appreciated that the tonometric method can now be modified in a fashion that provides the advantages of reduced equilibration time (with respect to saline) and without the need to recalibrate the sensor in vivo, or remove it for recalibration. In the improved method, and very generally, air is employed as the sampling medium and sampling can be done substantially continuously. The sampling medium air is aspirated from the walled sampling chamber of a tonometric catheter which has been inserted into the organ of interest (e.g., the gut). The $pCO_2$ of the aspirated sample is measured by employing a side-stream or main-stream, drift-free, non-dispersive infrared gas analyzer. The $pCO_2$ value obtained is then compared with either (1) the standard arterial bicarbonate value and/or (2) another direct or indirect measurement of a "global" or "systemic" physiologic value (e.g., arterial or venous pH; mixed venous bicarbonate; arterial oxygen saturation (e.g., as measured by pulse oximetry); arterial $pCO_2$; end tidal $pCO_2$; transcutaneous ($TCpCO_2$) $pCO_2$) in order to make a determination of the condition of the organ or if (A) a bicarbonate value must be obtained and/or (B) what, if any, clinical therapy or intervention may be necessary or appropriate with respect to oxygenation of the organ of interest.

In some embodiments, a Raman spectrometer may be employed, either in line or side stream, in place of the IR gas analyzer, as it will be appreciated by those skilled in the art that Raman spectroscopy offers distinct advantages over the more direct infrared-type measurements in certain applications.

A preferred indirect measurement of a "global" or "systemic" pH value is an end-tidal $CO_2$ value, or a transcutaneous $CO_2$ value.

However, the present invention has overcome these perceived and actual obstacles, and it successfully uses a gaseous sampling medium, such as air, along with known commercially available non-dispersive infrared spectrophotometry devices, resulting in high sample and measurement reliability, faster equilibration, thus allowing for faster and more frequent intermittent sampling, increased ease of use, and decreased sources of error, when compared to the prior use of a liquid sampling medium (such as saline), and a blood gas analyzer, for example.

Those skilled in the art will readily recognize the kind of non-dispersive, infrared gas analyzing devices contemplated by the present invention. Examples of these devices are those commercially available and marketed by such companies as Datex Instrumentarium Corporation or Novametrix Medical Systems, Inc., for example. Other examples of such devices and related equipment are discussed and disclosed in U.S. Pat. Nos. 4,233,513; 4,423,739; 4,480,190; 4,596,931; 4,859,858; 4,859,859; 4,907,166; 4,914,720; 5,042,522; 5,067,492; 5,095,913, the disclosures and drawings of all of which are hereby incorporated by reference herein.

Non-dispersive infrared gas analyzers in general are typically manufactured in either "side-stream" or "main-stream" configurations. In one, a sample of a volume of gas is taken from a patient's gas flow (such as respiratory gas flow, a tonometric sampling chamber gas flow, or both) and conveyed through a sample tube to the infrared sensor and analyzer; in such a device, the sample is not typically returned to the patient's gas flow. The other common type is the so-called in-stream or main-stream type, which has a sensor apparatus that mounts directly within the patient's gas flow conduit and senses and takes measurements as the gas flows past the sensor.

In an embodiment of the present invention, a pressure transmitting chamber in the form of a balloon is disposed about a catheter and encloses a volume between the wall of the pressure transmitting chamber and the catheter wall. That volume is filled with a pressure transmitting fluid or medium such as air or saline solution. As the pressure in the transmitting chamber varies in reaction to changes in the patient's internal pressure, e.g. IAP, that change in pressure is transmitted by the pressure transmitting fluid via the lumen in the catheter to a point outside of the patient for eventual monitoring and/or recordal by either medical personnel or machine.

In one embodiment, the pressure transmitting chamber communicates with a lumen inside the catheter via a portal which allows the pressure transmitting medium, e.g. air or a saline solution, to pass through the portal as internal pressure of a patient's organ, e g IAP bearing on the pressure transmitting chamber wall varies. The change in pressure on the pressure transmitting chamber wall is thereby communicated through the pressure transmitting chamber, through the portal and into and through the lumen by a pressure transmitting medium. In the case of an open system such as a catheter hooked up to a manometer, a change in pressure on the pressure transmitting chamber will cause a flow of pressure transmitting medium through the portal. By way of an example, an increase of pressure will compress the pressure transmitting chamber causing a change in volume. That change in volume is reflected by a flow of pressure transmitting medium out of the pressure transmitting chamber through the portal and into the catheter lumen eventually resulting in the change in the fluid level in the manometer.

In the case of a closed system such as one with a pressure transducer and saline solution as a pressure transmitting medium, a change in internal pressure may not produce a sizable change in volume of the pressure transmitting chamber, but rather compress the medium in the chamber with that change in pressure being transmitted through the portal up through the catheter lumen to the pressure transducer. The pressure transmitting medium can transmit this pressure to a pressure sensing means such as a pressure transducer or a manometer located, for example, at the proximal end of the catheter. The pressure transducer is used in the customary manner, known to those skilled in the art.

In an alternate embodiment, a pressure transducer can be installed in the pressure transmitting chamber and/or within the catheter lumen itself. A reading of the monitored pressure, e.g. the signal from the transducer, is transmitted through a portal communicating with the lumen and then through the lumen to a point outside the patient. There the signal from the transducer can be converted or translated, if necessary, to a machine or human readable form.

The invention can be used to monitor IAP by direct insertion into the gut by the use of conventional insertion techniques of a tonometric catheter. In one such use the invention is part of a nasogastric tonometer inserted into the stomach cavity. The pressure transmitting chamber is located in the organ or region where internal pressure is to be monitored.

The invention also encompasses the sensing of intraabdominal pressure while at the same time measuring intramucosal pH or pHi such as pHi of the gut. In one embodiment of the invention the catheter containing the lumen via which pressure is monitored contains a separate lumen by which pHi is monitored as described elsewhere in the application. Another lumen may allow flow of the pressure transmitting medium or the pressure signal. Alternately a single lumen may be shared for both pH and pressure monitoring.

The IAP may be monitored continuously while monitoring of the pHi is conducted. The preferred embodiment for this method is a catheter which comprises a pressure transmitting chamber communicating with a lumen for monitoring of the internal pressure and a separate walled sampling chamber to monitor pHi in fluid communication with the interior of a separate lumen within the same catheter.

In a separate embodiment of the invention a single chamber serves as both a pressure transmitting chamber for monitoring of internal pressure and as a sampling chamber for monitoring of pHi. In such an embodiment the wall of the chamber, i.e. the combined pressure transmitting and sampling chamber, comprises a membrane which is relatively permeable to the fluid or gaseous component to be sampled but sufficiently non-permeable to the pressure transmitting medium so that there is minimal transmission of pressure transmitting medium from the chamber across the chamber wall. The pressure gradient and loss across the chamber wall is thereby minimized. In this embodiment, the pressure transmitting medium can be the same as a saline sampling medium used to monitor the pHi. The saline sampling medium will sample the concentration and/or composition of at least one liquid fluid or gaseous fluid which permeates the chamber wall. The saline sampling medium can also be used to charge the chamber and create an inflated chamber for use as the pressure transmitting chamber by insufflating the catheter lumen and chamber with a quantity of the saline sampling medium. The saline sampling medium can then act as the pressure transmitting medium for transmitting pressure to a pressure sensor. By this embodiment, the internal pressure of the patient as well as the pHi can be monitored for the same in vivo location. The monitored pressure can then be used to correct pHi readings based upon the predictable effects that changes in pressure will have upon the concentration of gases which determine pHi.

In an embodiment of the invention internal pressure monitoring is used in conjunction with the monitoring of pHi to arrive at a correction factor applied to the determination of the pHi. The correction factor allows adjustment of the pHi based upon changes in the pressure of the gas such as $CO_2$ which permeates a $CO_2$ monitoring chamber. In this embodiment, the concentration of $CO_2$ in the sampling chamber is monitored to arrive at pHi as discussed in this application. The pressure of the $CO_2$ in the sampling chamber will be a function of the pressure of the $CO_2$ outside of the sampling chamber. The pressure of the $CO_2$ in the chamber will effect its concentration and hence the pHi. A change in the pressure of the $CO_2$ outside of the chamber will effect the pressure of the $CO_2$ measured inside the chamber. An increase in the internal pressure, e.g. IAP, will be transmitted through the sampling chamber wall and effect a change in the pressure of the $CO_2$ inside the sampling chamber with a concomitant change in the monitored pHi. By monitoring internal pressure such as IAP while also monitoring for pHi, the calculation of pHi can be adjusted based upon changes in internal pressure and the effect that those changes in internal pressures will have upon the gas pressures and hence concentration of measured gases.

For further understanding of the invention, its objects and advantages, reference may be had to the following specification, the accompanying drawings, and the information incorporated herein by reference. Also, see commonly assigned applications Ser. No. 719,097, filed Jun. 20, 1991; Ser. No. 994,721, field Dec. 22, 1992; Ser. No. 014,624, filed Feb. 8, 1993; and Ser. No. 08/035,020, filed Mar. 22, 1993, all of which are completely and expressly incorporated herein by reference.

BRIEF DESCRIPTION OF THE DRAWINGS

FIG. 1 is a plan view of an embodiment of a tonometric catheter;

FIG. 2A is a partial cross-sectional view of the tonometric catheter illustrating a first means for attachment of an electronic field effect transistor sensor;

FIG. 2B is a partial cross-sectional view of the tonometric catheter illustrating a second means of attachment of the field effect transistor sensor;

FIG. 3 illustrates the method of use of the tonometric catheter in measurement of the pH of the colon and also of the stomach, the specific embodiment illustrated for colonic measurement being that of FIG. 5 and the specific tonometric catheter for gastric measurement being that of FIG. 4;

FIG. 4 is another embodiment of the tonometric catheter with nasogastric tube;

FIG. 4A is a cross-sectional view of the tonometric catheter of FIG. 4 taken substantially along the line 4A—4A of FIG. 4;

FIG. 4B is a cross-sectional view of the tonometric catheter of FIG. 4 taken substantially along the line 4B—4B of FIG. 4;

FIG. 5 is yet another embodiment of the tonometric catheter having multiple sensing/sampling portions;

FIG. 5A is a cross-sectional view of the tonometric catheter of FIG. 5, taken substantially along the line 5A—5A of FIG. 5;

FIG. 11A is a cross-sectional view of the tonometric catheter/urinary catheter of FIG. 11, taken substantially along the line 11A—11A of FIG. 11.

FIG. 16A is a partial cross-sectional view of the tonometric catheter illustrating the attachment of a pressure transducer.

FIG. 17A is a cross sectional view of the catheter of FIG. 17 taken substantially along line 17a—17a.

FIG. 17B is a cross sectional view of the tonometric catheter of FIG. 17 taken substantially along line 17b—17b.

FIGS. 18A and 18B are a cross-sectional view taken along line 18a—18a of FIG. 18.

FIGS. 19 and 19A illustrate a tonometric catheter with a pressure sending apparatus installed.

FIG. 21 is a plan view of a wound drain catheter modified to embody the invention.

FIG. 21A is a side elevational view of the wound drain catheter of FIG. 21 taken along line 21A—21A of FIG. 21.

DETAILED DESCRIPTION

Figure 6:
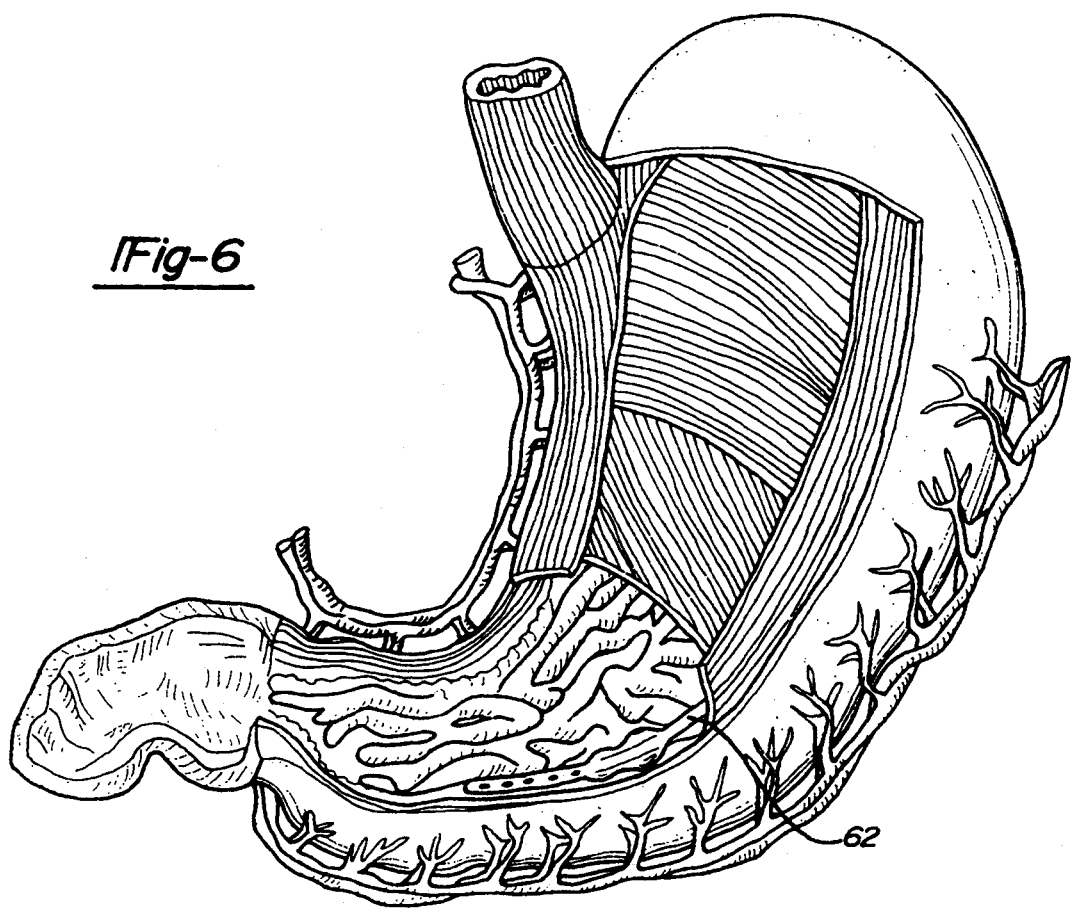
FIG. 6 is a detailed view illustrating the tonometric catheter of FIG. 4 in use within the stomach.

This application hereby expressly incorporates by reference, the disclosures and drawings of the following issued U.S. Patents: U.S. Pat. Nos. 4,221,567; 4,233,513; 4,273,636; 4,423,739; 4,576,590; 4,480,190; 4,596,931; 4,643,192; 4,671,287 4,859,858; 4,859,859; 4,907,166; 4,914,720; 5,042,522; 5,067,492; 5,095,913; 5,158,083; 5,174,290; and 5,186,172.

FIG. 1 illustrates a first embodiment of tonometric catheter 20. The tonometric catheter comprises a length of suitable tubing 22, one end 32 of which is closed, and the opposite end of which has a connector such as a luer-lock 24. Luer-lock 24 is adapted to receive a complementary fitting 26, which in turn couples through a second length of tubing 28 to a three-way stopcock 30. Three-way stopcock 30 may be used to selectively connect tubing 28 to various sources of irrigation or aspiration.

Adjacent the closed end 32, tubing 22 is perforated as at 34. A balloon-like tonometric catheter membrane 36 is fitted over the closed end so that the perforations 34 are enclosed, as illustrated. The tonometric catheter membrane 36 has an internal sleeve diameter at 38 which forms a tight fit with tubing 22. The preferred form of tonometric catheter membrane is polydimethylsiloxane elastomer. The membrane may be sealed to the tubing 22 with appropriate adhesive so that the tonometric catheter membrane is sealed in a closed relationship to the outer wall of tubing 22, thereby forming a sampling chamber 40 adjacent closed end 32. The tonometric catheter membrane has a certain elasticity to allow the membrane to expand when filled with an aspirating fluid in order to contact the wall of the organ under examination, as will be explained below.

The membrane 36 is preferably constructed such that at least a portion of it is selectively permeable to the gas or fluid property of interest. In a preferred embodiment, it is selectively permeable to hydrogen, oxygen, or $H^+$, so that pH, $pCO_2$ and/or $pO_2$ can be measured. It is also preferably impermeable to other materials that would interfere with the desired measurements, such as other gases, proteins, and the like. In a highly preferred embodiment, an ion-selective membrane is employed.

Bonded to either the inner wall or the outer wall of tubing 22 are one or more sensors 42 for detecting a property indicative of pH and/or temperature. Two such sensors are illustrated in FIG. 1, bonded to the outside wall of tubing 22 with suitable adhesive. FIGS. 2A and 2B illustrate two alternate means of sensor attachment, FIG. 2A illustrating the sensor attached to the inner wall of tubing 22 and FIG. 2B illustrating the sensor attached to the outer wall of tubing 22.

In a preferred embodiment, at least a portion of the tubing, but not all of it, is made of a $CO_2$ impermeable material, such as those based on polyurethanes, PVC's, or polyester elastomers derived from the reaction of dimethylterephtalate 1,4-butanediol and $\alpha$-hydro-$\Omega$-hydroxypoly (oxytetramethylene). In a highly preferred embodiment, this is a material such as Hytrel, sold by duPont.

For purposes of sensing temperature, thermistor devices are presently preferred. For sensing properties indicative of pH chemically responsive field effect transistors or "Chemfets" may be employed. In this regard, Chemfet sensors 44 have been illustrated in FIGS. 2A and 2B. Chemfet sensor 44 comprises a field effect semiconductor device 46, which is encapsulated in a solution impervious material 48, such as a polymerized epoxy resin. The encapsulation material 48 in turn may be encapsulated in a housing 50 (FIG. 2A). Semiconductor device 46 is electrically coupled by bonding wires 52 to a terminal 54. Suitable electrical conductors such as conductor 56 are attached to terminal 54 for electrically communicating between the Chemfet device 44 and the electronic circuitry described below in connection with FIG. 9. Conductor 56 is preferably routed through tubing 22 and exits through a sealed aperture at or near the luer-lock end of tubing 22, as at 58. A more detailed description of a suitable electronic sensor may be found in U.S. Pat. No. 4,020,830 to Johnson, entitled "Selective Chemical Sensitive FET Transducers," incorporated herein by reference. In order to allow a solution to contact the chemically sensitive surface of semiconductor device 46, tubing 22 may be provided with an aperture 60 when implementing the embodiment of FIG. 2A. Such an aperture is not needed in the embodiment of FIG. 2B, since the semiconductor device 46 is exposed to sampling chamber 40 by virtue of the external mounting configuration.

The sampling chamber 40 can be filled with an aspiration or sampling medium (gaseous or liquid) that is used to absorb or otherwise provide a means for incorporating and delivering or measuring the fluids or gases of interest. Such a medium is selected depending upon many factors, including the properties of the fluids or gases of interest, the type of sensor 42 employed, and the type of calibration that is necessary. Such mediums include air, bicarbonate solutions, bicarbonate-buffered solutions, phosphate-buffered solutions and saline solution. It might be noted that gases often behave as fluids and are therefore frequently considered to be fluids.

As noted above, when the sensor employed does not require frequent recalibration, the need for the sampling chamber 40 to be in communication with the proximate end of the tonometric catheter (that remains outside the patient) may be eliminated since no aspiration is needed. However, in many instances such communication may still be desirable as aspiration may be required to calibrate the sensor or sensors, to replace the aspirating or sampling medium with a fresh medium, and to incorporate the gas or gases of interest.

Figure 16:
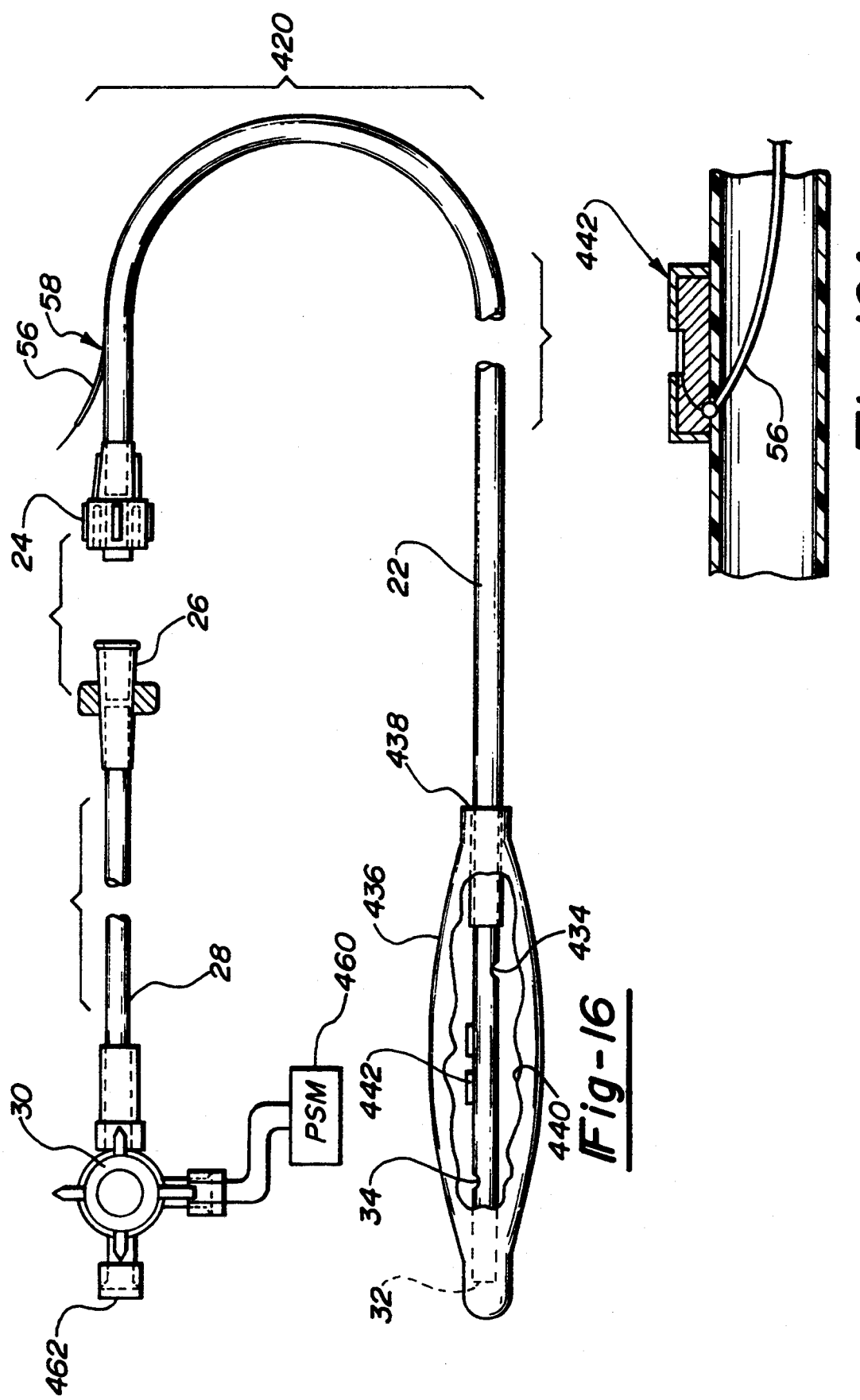
FIG. 16 is a plan view of an embodiment of a pressure monitoring catheter with a cut away section.

An embodiment of the tonometric catheter configured for the sensing of internal pressures, especially IAP, is illustrated in FIG. 16. Elements in common with FIG. 1 are given the same reference numerals. The pressure sensing catheter 420 comprises a length of suitable tubing 22, one end 32 of which is closed and the opposite end of which has a connector such as a luer-lock 24. Luer-lock is adapted to receive a complimentary fitting 26 which in turn couples to a second length tubing 28 to a three way stopcock. Three way stopcock 30 may be used to selectively connect tubing 28 to various sources of irrigation, aspiration or to a pressure sensing means or monitor.

Adjacent to closed end 32, tubing 22 is perforated as at 434. A balloon like tonometric catheter membrane 436 is fitted over the closed end so that the perforations 434 are enclosed as illustrated. Pressure transmitting catheter membrane 436 has an internal sleeve diameter at 438 which forms a tight fit with tubing 22. The preferred form of tonometric catheter membrane for pressure sensing applications is a relatively gas impermeable and saline impermeable material such as a conventional balloon used in angioplasty. The balloon wall can be made of a latex, silicone, polyurethane or polyethylene.

For certain applications a PVC material may also be used. Tonometric catheter balloons of the type suitable for use in the present invention are available from Tonometrics, Inc., Worcester, Mass., U.S.A. The membrane may be sealed to tubing 22 with appropriate adhesive known to the art such as silicone RTV type adhesive so that the tonometric catheter membrane is sealed in a closed relationship to the outer wall of tubing 22 therefore forming a pressure transmitting chamber 440 adjacent closed end 32. The pressure transmitting tonometric catheter membrane has a certain elasticity to allow the membrane to expand when filled with a pressure transmitting medium such as air, or a saline solution. The pressure transmitting medium allows the transmission of pressure changes as reflected by the movement of pressure transmitting tonometric catheter membrane 436 to be transmitted through the pressure transmitting chamber 440 and registered upon a pressure sensing means as explained below. As an alternative to the balloon-type chamber illustrated in FIG. 16 a cuff-type chamber may be used, similar to the chamber on a pulmonary arterial catheter.

A membrane 436 is preferable constructed such that in one embodiment it is relatively impermeable to the pressure transmitting medium as well as to normally occurring gaseous and liquid fluids encountered in vivo. For another embodiment, the membrane 436 can be silicone which is permeable by $CO_2$ through diffusion in vivo but relatively impermeable to a saline solution used both for $CO_2$ sampling and pressure transmitting purposes.

The pressure transmitting medium is in pressure transmitting communication with the interior of tubing 22 such as through perforation 434. Tubing 22 is filled with pressure transmitting medium along its entire length. Tubing 28 is also filled with pressure transmitting medium throughout its length. By filled it is meant that the system from pressure transmitting chamber 440 through tubing 22 through tubing 28 up to pressure sensing means 460 is filled with a single uninterrupted volume of pressure transmitting medium, substantially devoid of discontinuities or impurities having different compressibilities than the pressure transmitting medium. By way of example, when the pressure transmitting medium is a saline solution, the system should be substantially devoid of gas bubbles or gas pockets which would inhibit the accurate transmission of pressure through the pressure transmitting medium from pressure transmitting chamber 440 to pressure sensing means 460. To monitor the temperature and temperature changes a thermistor may be located either within the pressure transmitting chamber or the catheter lumen. Temperature readings can be used to correct changes in pressure based on temperature dependent effects.

Preferred embodiments for pressure sensing means 460 are pressure sensing transducers such as Gould disposable model TXXR or a manometer such as a CVP manometer by Abbott Laboratories, North Chicago, Ill., USA which is designed for intermittent or continuous monitoring of central venous pressure.

The preferred method of use of the tonometric catheter of FIG. 16 involves its insertion after assembly into the patient so that the pressure sensing chamber 440 is within the area to be monitored for pressure, e.g. the stomach. The tonometric catheter 20 is then charged with pressure transmitting medium in the case of a gaseous pressure sensing medium. In the embodiment utilizing liquid pressure transmitting medium, such as a saline solution the system may be precharged before insertion with pressure transmitting medium so as to be substantially free of gaseous impurities which may diminish the systems ability to accurately transmit pressure changes throughout the system. The system should not be charged before insertion to a pressure which would significantly expand chamber 440 and hinder insertion.

In an embodiment utilizing a gaseous pressure transmitting medium, the system is charged after insertion by inflation of the balloon with gas such as via stopcock portal 462 so as to inflate pressure transmitting chamber 440 sufficiently to allow pressure transmitting tonometric catheter membrane 436 to be impinged upon and transmit changes in pressure to the pressure transmitting medium in chamber 440. The chamber should not be over inflated so as to add unnecessary volume to chamber 440 which may add unwanted pressure to the internal organs of the patient. In adult patients it has been found that inflation of the system of up to three milliliters of gaseous pressure transmitting medium has provided satisfactory results. The volume of medium inflated should be carefully measured. Should inflation be necessary the same volume may be inflated allowing comparisons of pressure readings. By having the same volume in the systems, comparisons can be made according to the gas law $PV=nRT$. Once the system has been inflated and stopcock opening 462 sealed, pressure sensing means 460 may be calibrated and/or zeroed. Changes in internal pressure of the patient act upon membrane 436 which in turn alters the volume and/or pressure of chamber 440. The change in volume or pressure of chamber 440 is transmitted by pressure transmitting medium upon the pressure sensing means 460 which will thereby reflect changes in the internal pressure of the patient.

The pressure sensing means 460 need not be operably connected to the stopcock and can be connected anywhere along the system where it is in pressure sensing communication with the pressure transmitting medium. In one embodiment pressure sensing means 460 may be connected to the luer-lock 24 after the system has been charged with pressure transmitting medium.

In an alternative embodiment also illustrated in FIG. 16 by way of phantom line additions, pressure sensing means may be placed within the system such as by way of a pressure transducer 442 placed within the pressure transmitting chamber 440. Turning to FIG. 16A, pressure transducer 442 would then be operably connected to conduit 56 so as to communicate the pressure transducer's signal via conduit 56 outside of the system via aperture 58 and then to a proper translation and/or display apparatus (not shown). Aperture 58 should be such that pressure sealing contact with conduit 56 is maintained by tubing 22 so that tubing 22 may be charged with pressure transmitting medium without leakage at aperture 58. In a preferred embodiment, pressure transducer 442 is a microelectronic device whose output is communicated via a conduit 56 in the form of an electrically conductive wire.

The preferred method of use of the pressure sensing catheter is to have the catheter assembly completed before insertion into the patient. The catheter is inserted via conventional nasogastric techniques into the gut of the patient. The catheter assembly in the proper configuration can be utilized for monitoring pressure in a variety of locations. These locations include the stomach, the large and/or small intestines and the rectum. In addition, the pressure sensing chamber may be located so as to rest against the surface of an organ such as the liver or kidney to monitor the pressure exerted upon that organ to assist in the diagnosis of the effect of pressure upon that organ's function. In addition, the system could be used to monitor esophageal pressure. In general, the system can be used to monitor whether or not the various sphincters throughout the body are working to seal off chambers by monitoring, e.g. pressures upon either side of the various sphincters. Areas other than the gut can be monitored via this apparatus and method including intercranial pressure.

For certain monitoring applications, the configuration of the catheter can be changed, for example the pressure sensing chamber may be applied for use on a feeding catheter. A pressure sensing chamber could also be installed on a wound drain catheter such as a Jackson-Pratt catheter where the pressure sensing chamber was resting against the liver. In such an embodiment a single catheter can be simultaneously draining as well as performing pHi, pressure, and/or temperature monitoring.

FIG. 21 shows a closed wound drainage catheter modified to also monitor internal pressure and/or pH. Tubing 522 has a plurality of internal lumens. One internal lumen 524, in communication with the drainage area 528, can be hooked up to a conventional drainage reservoir for a closed wound drainage system such as the Jackson-Pratt closed wound drainage system supplied by American Hospital Supply Corporation as is well known to those skilled in the art. Lumen 524 is in fluid communication with wound drainage apertures 530. Turning to FIG. 21A, lumen 524 is non-communicating with lumen 526. Lumen 526 communicates with combined pressure transmitting and sampling chamber 540. Chamber wall 542 is preferably made of a silicone membrane which allows for diffusion of $CO_2$ for measurement of pHi as discussed above. Lumen 526 will therefore communicate with both a pressure sensing means such as a manometer or pressure transducer as well as sensor means to monitor and calculate the pHi of the subject. A single medium such as saline solution can serve as both a sampling medium and a pressure transmitting medium. The flat surface of the bottom of the chamber 540 allows the membrane 542 to lie against an organ, such as the liver. While wound drainage occurs the pressure and pHi of the monitored liver surface can be monitored.

Pressure may be continuously or intermittingly monitored. The catheter may be left in the patient for a period of time and the pressure continuously monitored such as by using a plotter to record a graph of pressure over time. Alternately the pressure readings may be taken at discrete time intervals, e.g. every 30 minutes. Use of the described techniques and apparatus in the stomach can avoid transcutaneous monitoring of pressure allowing longer term monitoring while avoiding invasive techniques and their attendant risks such as infection.

The use of a pressure transmitting chamber on a catheter can also serve as a positioning mechanism. The pressure transmitting chamber can be inserted into the patient and its location confirmed through various techniques such as its inflation and monitoring of the pressure, manipulation of the patient such as manually applying pressure to a selected location and monitoring any result in increase in pressure or auscultation of air as it is being insufflated. The use of the pressure monitoring system as a position mechanism may eliminate the need for an x-ray to confirm the location of either the pressure transmitting chamber or other apparatus on the same catheter.

In the preferred method, the catheter is inserted during a period of quiescent motor activity with no evidence of the migrating motor complex. Certain phases of the migrating motor complex are characterized by rapid convulsions of the stomach and/or intestine which reduce the effectiveness of the pressure monitoring apparatus. In certain situations, the pressure monitoring apparatus can be used to monitor the phase of migrating motor complex. During the phases that have rapid convulsions, the pressure readings can be run through a signal detection algorithm where rapid fluctuations and peaks trigger a reading that a certain phase of the complex is present. The algorithm can be programmed to either mark certain pressure readings as unusable due to excessive motor activity or be used itself as a monitor of motor activities.

Another embodiment of the tonometric catheter is illustrated in FIGS. 4, 4A and 4B. As illustrated, the tonometric catheter is appropriately configured to also serve as a nasogastric sump, either with or without gastric suction. With reference to FIG. 4, the tonometric catheter 20a comprises a multipassage tubing 62 which defines three individual noncommunicating (between each other) passageways or lumens, an air lumen 64, an optional suction lumen 66 and a tonometric catheter lumen 68. A tonometric catheter membrane, similar to that previously described, is attached at an intermediate location on tubing 62, allowing a portion of the tubing to extend beyond the end of membrane 36 to define the nasogastric sump 70. Tubing 62 is provided with a plurality of perforations 72 which communicate between tonometric catheter lumen 68 and the sampling chamber 40 defined by membrane 36. If desired, one or more sensors 42 can be included in accordance with the above teachings, in which case a suitable conductor 56 may be routed through tonometric catheter lumen 68 to exit at sealed aperture 58.

The nasogastric sump portion 70 is suitably provided with a plurality of openings 74 through which the stomach may be aspirated.

At the opposite end of tubing 62 the tubing splits to form three separate connections. Air lumen 64 communicates with air lumen passageway 76, suction lumen 66 connects with suction lumen passageway 78 and tonometric catheter lumen 68 communicates with tonometric catheter lumen passageway 80. The tonometric catheter lumen passageway is fitted with three-way stopcock 30, similar in function and purpose to the three-way stopcock 30 described in connection with FIG. 1. If desired, a quick connect fitting 82 may be used to couple the suction lumen passageway 78 with an aspiration source. As illustrated, the quick connect fitting preferably has angularly cut ends and a slightly enlarged midsection, making it easy to insert into the end of passageway 78 and also into the aspiration hose coupling (not shown). The enlarged midsection helps form a seal with the adjoining passageways. Preferably the quick connect fitting is fabricated of disposable plastic.

Figure 17:
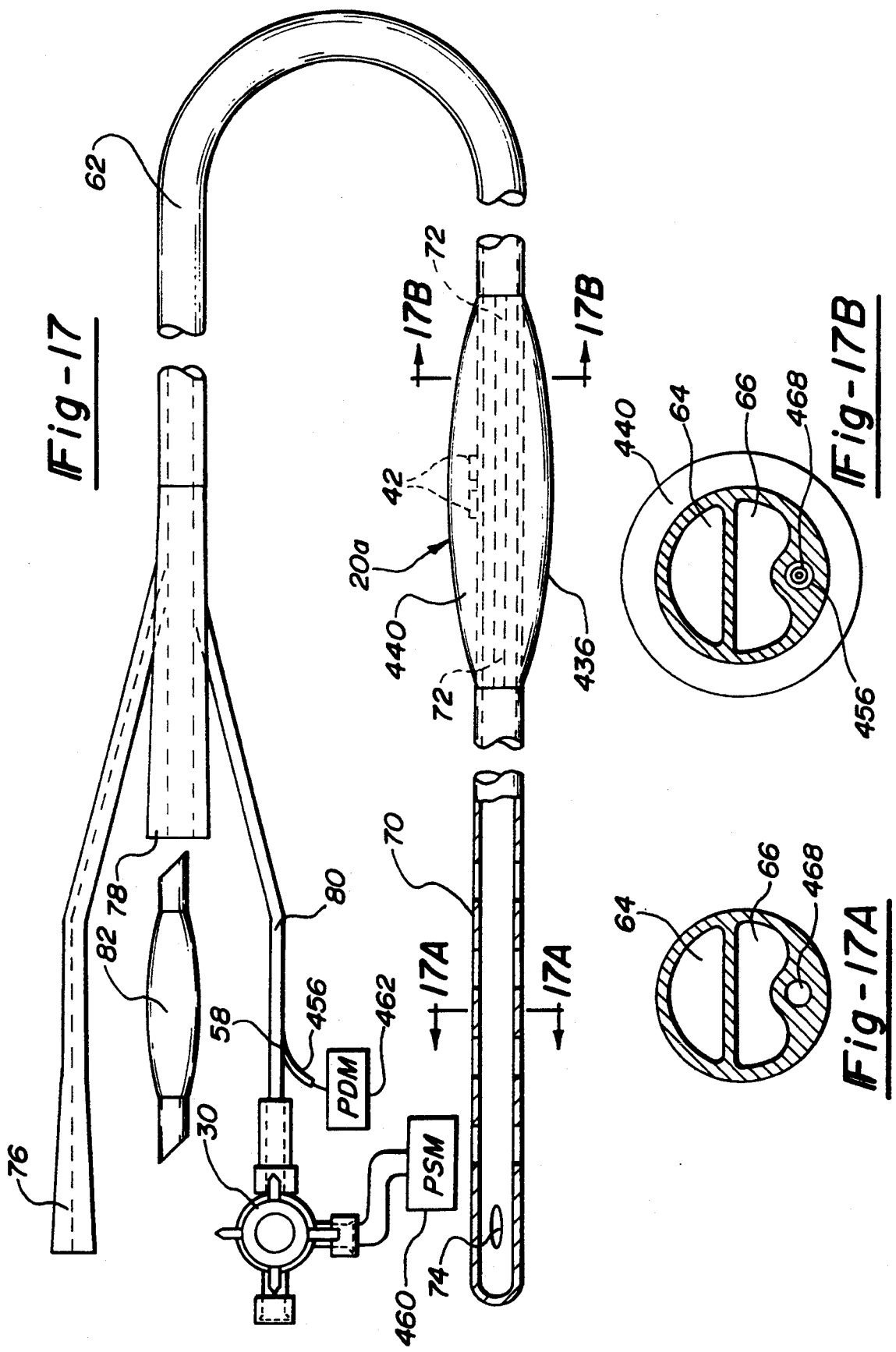
FIG. 17 is an embodiment of a catheter for internal pressure sensing with a nasogastic tube.

Turning to FIG. 17 another embodiment of a pressure sensing tonometric catheter is illustrated for sensing the internal pressure such as the IAP of a patient. The catheter illustrated in FIG. 17 is configured to also serve as a nasogastric sump either with or without gastric suction. Identical elements of the tonometric catheter of FIG. 4 are identified with the same reference numerals. Multi-passage tubing 62 defines three individual non-communicating (between each other) passageways or lumens, air lumen 64, an optional suction lumen 66, and a pressure transmitting medium lumen 468. A tonometric catheter membrane, similar to that previously described with reference to FIG. 16 is attached in an intermediate location in tubing 62, along a portion of the tubing so as to allow tubing 62 to extend beyond the end of membrane 436 to define the nasogastric sump 70. Tubing 62 is provided with a plurality of perforations 72 which communicate between pressure transmitting lumen 468 and the pressure transmitting chamber 440 defined by membrane 436. If desired, one or more pressure transducers or sensors 42 can be included in accordance with the above teachings, in which case a suitable conductor or conduit 456 may be routed through pressure transmitting lumen 468 to exit at sealed aperture 58. Conductor 456 can be figured so as not to compromise pressure transmitting lumen 468 in its ability to allow a flow of pressure transmitting medium through lumen 468.

The nasogastric sump portion 70 is suitably provided with a plurality of openings 74 through which the stomach may be aspirated.

At the opposite end of the tubing 62 the tubing splits to form three separate connections. Air lumen 64 communicates with air passageway 76. Suction lumen 66 connects with suction lumen passageway 78 and pressure transmitting lumen 468 communicates with pressure transmitting lumen passageway 80. The pressure transmitting lumen passageway 80 is fitted with a three way stopcock 30 similar in function and purpose to the three way stopcock described above especially in connection with FIG. 16.

In use the pressure transmitting lumen 468 is purged of potential contaminants and either precharged with pressure transmitting medium before insertion or preferably charged after insertion. Once pressure transmitting lumen 468 is properly charged along with pressure transmitting passageway 80, pressure sensing means 460 may be operably associated via the stopcock 30 with pressure transmitting passageway 80 so as to register changes in the IAP of the patient. Changes in the internal pressure, such as the IAP, of the patient will be communicated to pressure sensing means 460 in the manner described in connection with FIG. 16. Alternately to pressure sensing means 460, pressure transducer or sensor 42 may be operably associated with pressure display means 462 via conduit or conductor 56 to display changes in the patients internal pressure. Pressure display means 462 may be of the type known to those skilled in the art such as a cathode ray tube which can display in graphic or numerical format or a plotter which will graph on paper in X-Y coordinates.

Yet another embodiment of the tonometric catheter is illustrated in FIGS. 5 and 5A. This embodiment is a multiple tonometric catheter embodiment employing a tubing 84 having a plurality of passageways or lumen as shown in the cross-sectional view of FIG. 5A. Specifically, tubing 84 includes an air lumen 86a which communicates with the endmost tonometric catheter 36a and three additional tonometric catheter lumens 86b, 86c and 86d, which communicate respectively with tonometric catheters 36b, 36c and 36d. As with the other embodiments, each tonometric catheter may be provided with one or more sensors such as sensors 42. A radiopaque tungsten plug 88 is positioned within each of the three tonometric catheter lumen 86*b*, 86*c* and 86*d* adjacent the distal end of each tonometric catheter, serving to block the remainder of the tonometric catheter lumen passageway and thereby ensuring that fluid pressure introduced into each tonometric catheter lumen will cause the associated tonometric catheter to balloon outwardly as required during use. Similarly, a radiopaque tungsten rod 90 is fitted as a plug in the end of air lumen 86*a*, serving to terminate the end of the air lumen passageway. Being radiopaque, the tungsten plugs and tungsten rod aid in properly positioning the tonometric catheters by being visible under fluoroscope or x-ray. In addition, if desired, tubing 84 can be provided with a radiopaque stripe along all or part of its length.

At the proximal end of tubing 84 the lumen 86*a*–86*d* diverge to define four separate tubes 92*a*–92*d*. Each tube is fitted with a three-way stopcock similar to those described above. Each sampling connector may optionally be coded numerically by color, etc. While four approximately equally spaced tonometric catheters have been illustrated in FIG. 5, it will be understood that the invention can be modified to include a greater or fewer number of tonometric catheters at different spacing as required for a particular application. It will also be understood that some or all of the tonometric catheters can include one or more sensors coupled to conductors 56, each preferably routed through the corresponding lumen passageway.

Figure 19:
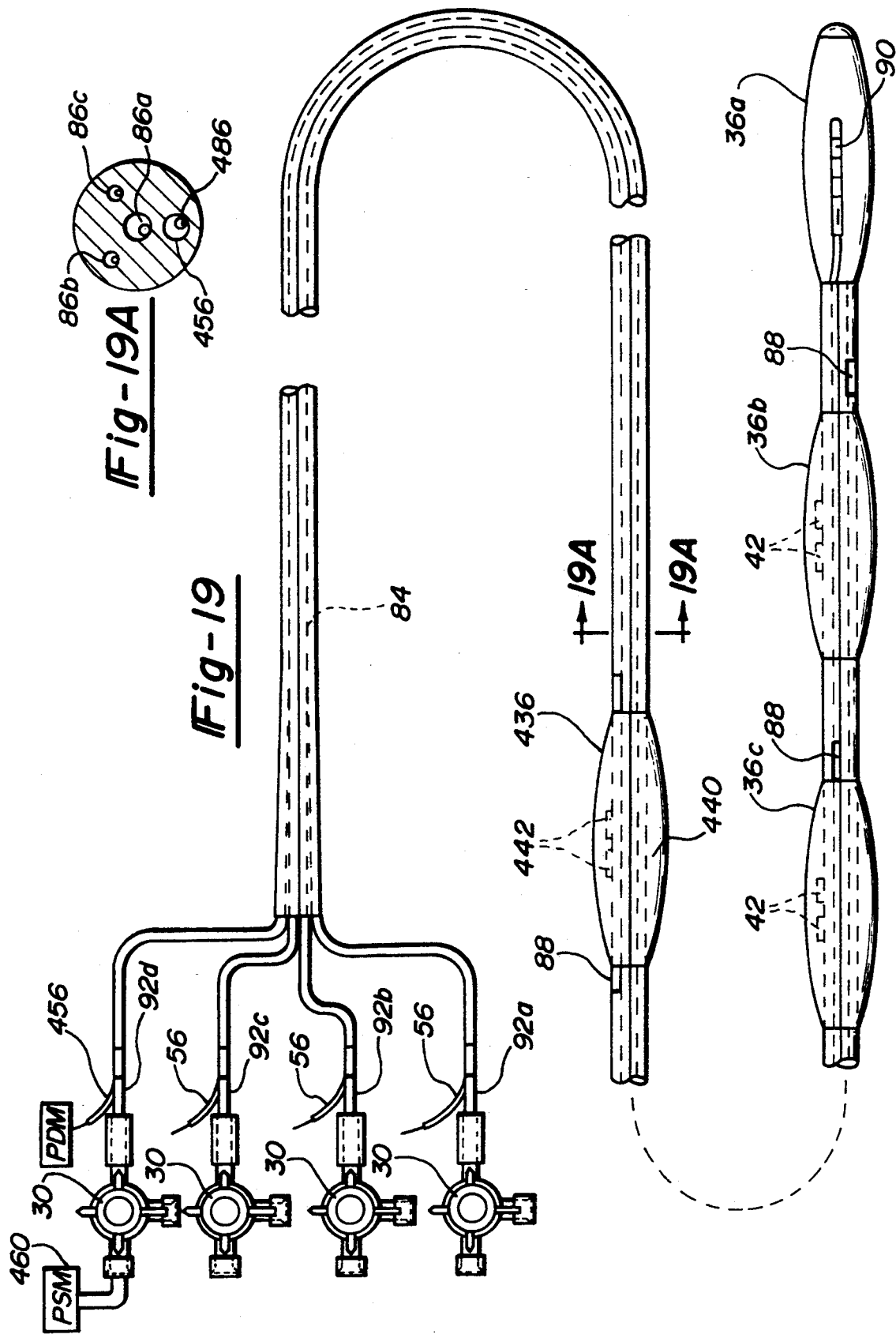

Referring now to FIG. 19, an alternate embodiment of the invention is illustrated. With reference to FIG. 5, the same elements are given the same reference numerals as in FIG. 19. The device of FIG. 5 has been modified as shown in FIG. 19 to include means for sensing internal pressure of a patient such as IAP. In this embodiment, a multiple tonometric catheter is shown employing tubing 84 having a pluralities of passageways or lumens which do not communicate with one another as shown in the cross sectional view of FIG. 19A. Specifically, tubing 84 includes an air lumen 86 which communicates with the end most tonometric catheter 36A and two additional tonometric lumens 86*b* and 86*c* which communicate respectively with tonometric catheters 36*b* and 36*c*. As explained above, each tonometric catheter may be provided with one or more sensors such as sensors 42. A radiopaque plug 88 is positioned within each of the tonometric catheter lumens 86*b* and 86*c* adjacent the distal end of each tonometric catheter serving to block the remainder of the tonometric catheter lumen passageway and thereby insuring that the fluid pressure introduced into each tonometric catheter lumen will cause the associated tonometric catheter to balloon outwardly as required during use.

Tubing 84 includes pressure transmitting lumen 486 which communicate with pressure transmitting chamber 440 created by membrane 436 to create a pressure sensing tonometric catheter similar to that described in FIG. 16.

At the proximal end of tubing 84, pressure transmitting lumen 486 diverges from lumens 86*a*, 86*b*, and 86*c*. As described with respect to other embodiments the pressure sensing tonometric catheter may be operably connected to a pressure sensing means 460 via pressure transmitting lumen 486 by means of a pressure transmitting medium. Alternatively, a pressure transducer 442 may be located within the pressure transmitting chamber 440 and operably connected with a signal converting and display means 462 via conductor 456. The radiopaque plug 88 is positioned in pressure transmitting lumen 486 adjacent the distal end of the pressure transmitting chamber.

Figure 9:
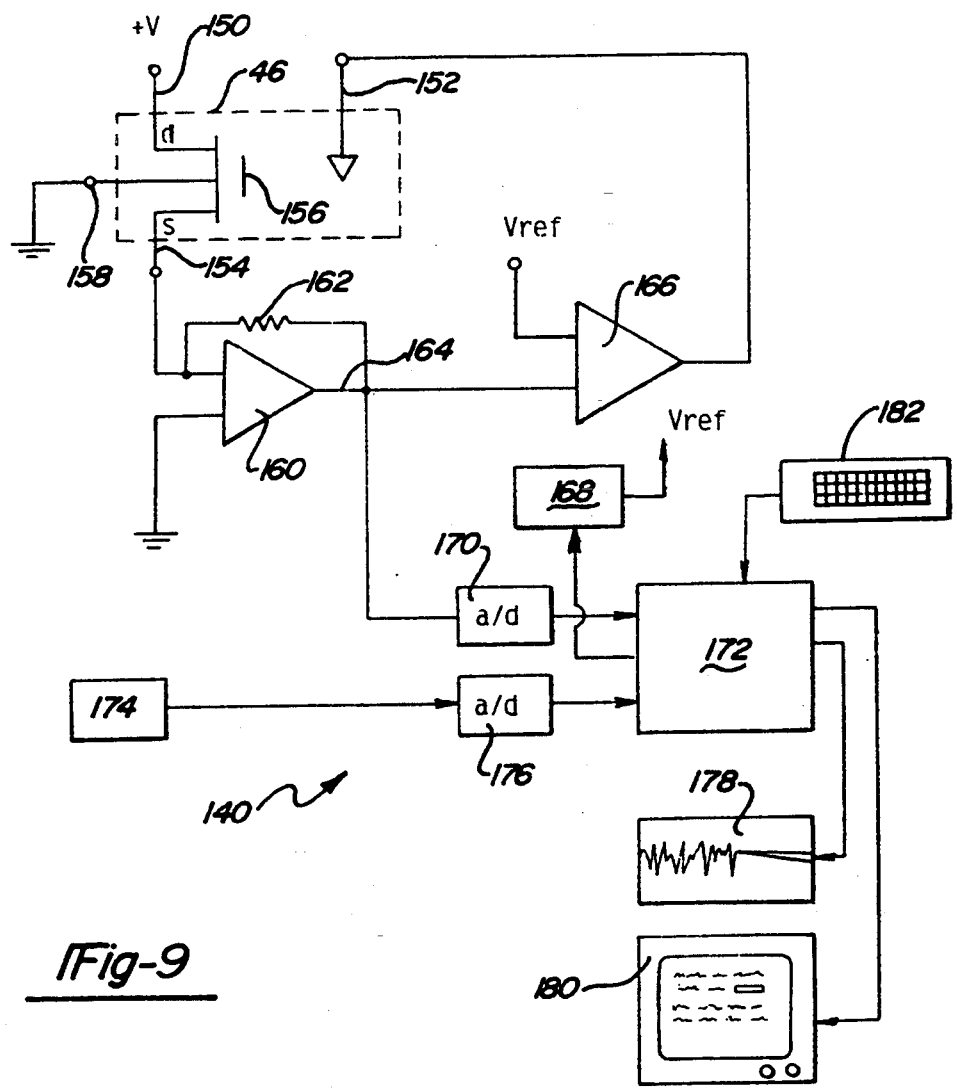
FIG. 9 is an electrical schematic diagram illustrating one embodiment of electronic circuit in accordance with the invention.

Referring now to FIG. 9, a suitable electronic monitoring circuit will now be described. In FIG. 9 CHEMFET semiconductor device 46 has been shown schematically by the equivalent circuit model enclosed in dotted lines. The device 46 thus comprises drain electrode 150, source electrode 152 and reference electrode 154. The chemically selective system, such as a membrane system is depicted diagrammatically at 156. The substrate is grounded as at 158.

Source electrode 154 is coupled to an input lead of operational amplifier 160 which includes feedback network diagrammatically depicted at 162. Operational amplifier 160 senses the drain source current flowing through device 46 and converts this signal into a voltage signal which is output on lead 164. The drain source current changes in accordance with changes in the chemical system under test. More specifically, as the $pCO_2$ level changes in the fluid exposed to device 46, the drain source current changes accordingly. Hence the output voltage signal on lead 164 is likewise an indication of the $pCO_2$ level of the organ under test. This voltage signal on lead 164 is coupled to an input of comparator 166 which also receives a reference voltage $V_{ref}$, which may be supplied using a voltage divider network (not shown) or which may alternatively be provided by a digitally controlled voltage source 168. The output of comparator 166 is fed to reference electrode 154 to provide a stable reference bias voltage. If a digitally controlled voltage source is used, this reference voltage can be adjusted and calibrated by a computer circuit yet to be discussed. The voltage signal on lead 164 is also fed to an analog to digital convertor 170, which is in turn coupled to a microprocessor-based microcomputer 172.

In order to automatically determine the pH of the wall of the hollow viscous organ under test, a separate gas analyzer sensor 174 is used to determine the bicarbonate concentration in the arterial blood of the patient. The output of sensor 174 is coupled through analog to digital convertor 176 to microcomputer 172. Microcomputer 172 is preprogrammed to determine or calculate the pH of the organ wall using the values provided by analog to digital convertors 170 and 176. Conversion of $pCO_2$ measurements can be converted into pH measurements automatically by microcomputer 172 using various equations and references disclosed herein or others well-known in the art.

Although many different types of output devices may be employed, strip chart recorder 178 and CRT monitor 180 have been illustrated. Strip chart recorder 178 and monitor 180 are coupled as output devices to microcomputer 172. Strip chart recorder 178 offers the advantage of developing an easily readable, permanent record of the fluctuations in organ wall pH. Monitor 180 offers the advantage of providing digital readout of the pH value as well as displaying the upper and lower excursions of pH fluctuation. If desired, microcomputer 172 can be instructed and/or preprogrammed using keyboard 182 to compare the instantaneous pH value with doctor-selected upper and lower alarm limits. If the measured instantaneous pH fluctuates outside those limits, microcomputer 172 can sound an alarm to alert hospital staff.

While a single semiconductor device 46 has been illustrated in conjunction with the electronic circuit of FIG. 9, the circuit may be readily adapted for use with a plurality of semiconductor devices in order to measure the pH at different locations substantially simultaneously. In such an embodiment, the data coming from each sensor can be fed to a separate I/O port of microcomputer 172. In the alternative, a single I/O port can be used with the individual input signals being time multiplexed.

Figure 7:
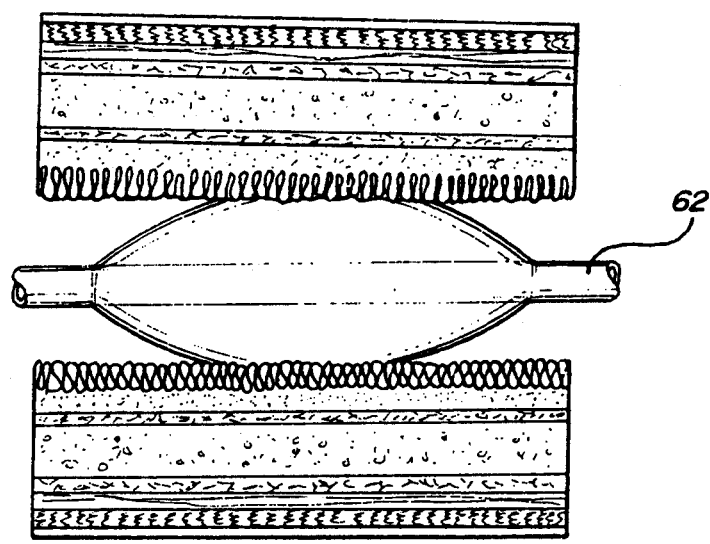
FIG. 7 is a detailed view illustrating the tonometric catheter of FIG. 5 in use within the colon.
Figure 8:
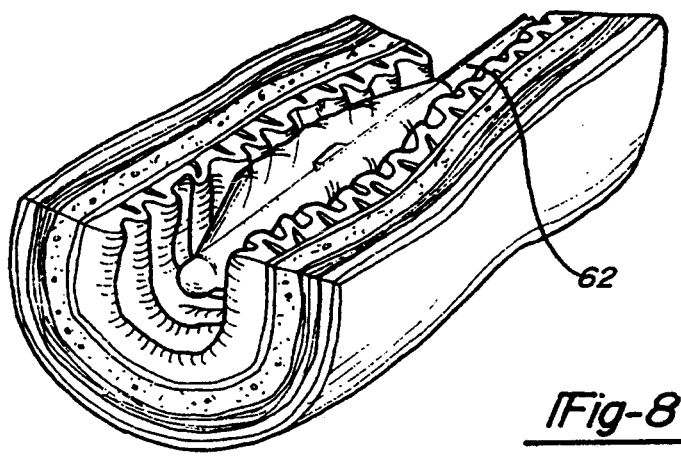
FIG. 8 is a similar view illustrating the tonometric catheter of FIG. 1 in use within the colon.
Figure 10:
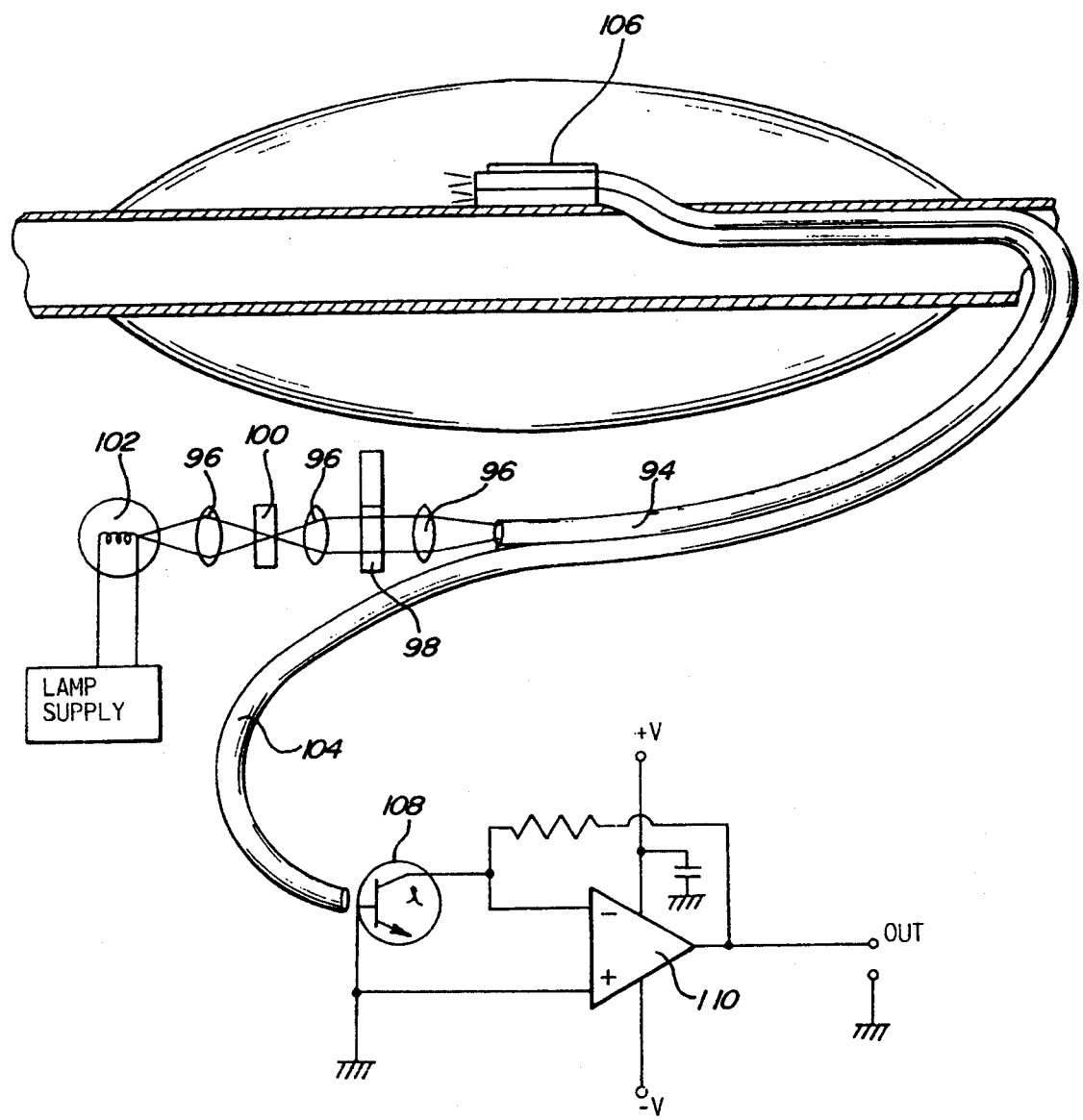
FIG. 10 is an electrical schematic diagram illustrating another embodiment of the optical measurement of pH in accordance with the invention.

As an alternative to electronic pH sensors, the invention may also be practiced using optical sensor technology. Referring to FIG. 10, the presently preferred optical sensor embodiment uses a first fiber optic cable 94 which is optically coupled through a series of lenses 96, selectable color filters 98 and heat absorber 100 to an illumination source 102, such as a 100 watt tungsten-halogen lamp. Fiber optic cable 94 is routed through the tonometric catheter lumen in a fashion similar to the conductor 56 of the above-described embodiments, with the end thereof protruding through the tubing and into the sampling chamber 40. A second fiber optic cable 104 is routed parallel to the first fiber optic cable 94, with one end protruding through the tubing and held in place adjacent the end of first cable 94 with a collar 106. Collar 106 may be adhesively bonded to the outside wall of the tubing. The opposite end of second fiber optic cable 104 is positioned for optically coupling with a phototransistor 108 which is electrically connected to an operational amplifier circuit 110. The operational amplifier circuit can be coupled to an analog to digital converter, such as A/D converter 170 of FIG. 7.

In use, fiber optic cable 94 illuminates a region within the sampling chamber 40 which is filled with a sampling fluid containing a colorimetric pH indicator. The illumination from fiber optic cable 94 reflects from the molecules suspended in the pH indicator solution, with some of the reflected illumination passing back through second fiber optic cable 104 to the phototransistor. By selecting the appropriate filter 98, a monochromatic illumination or illumination of otherwise known spectral content is employed to illuminate the colorimetric pH indicator solution. When the color of the filtered illumination matches that of the indicator, the illumination is absorbed and a low illumination signal is received at the phototransistor. When a pH change causes a color change in the indicator away from the color of the filtered illumination, more illumination is reflected back to the phototransistor, with an attendant increase in detected signal output. In this fashion, the proper selection of indicator dye and illumination filtration can be used to detect pH ranges. For a further description of fiber optic pH sensor technology, refer to G. G. Vurek "A Fiber Optic pCO$_2$ Sensor," *Annals of Biomedical Engineering*, Vol 11, pp. 499–510, 1983, which is available from Pergamon Press, Ltd., and is expressly incorporated herein by reference.

While the preferred embodiments have been disclosed in connection with monitoring of the gastrointestinal tract and the urinary and ureteric tracts it will be appreciated that its principles are applicable to other hollow internal organs to monitor pH and hence perfusion of those organs. Also while several presently preferred detailed constructions for tonometric catheters have been disclosed, it will be appreciated that other constructions may be developed which are equally suitable. The disclosed constructions are presently preferred for the reason that they are readily fabricated using existing available materials. Other embodiments may include other, but equivalent materials for the tonometric catheter membrane and/or connective tubing. They may also differ in the specific fabrication details. As an example, the sampling chamber may be eccentric rather than symmetric about the connective tubing.

Figure 12:
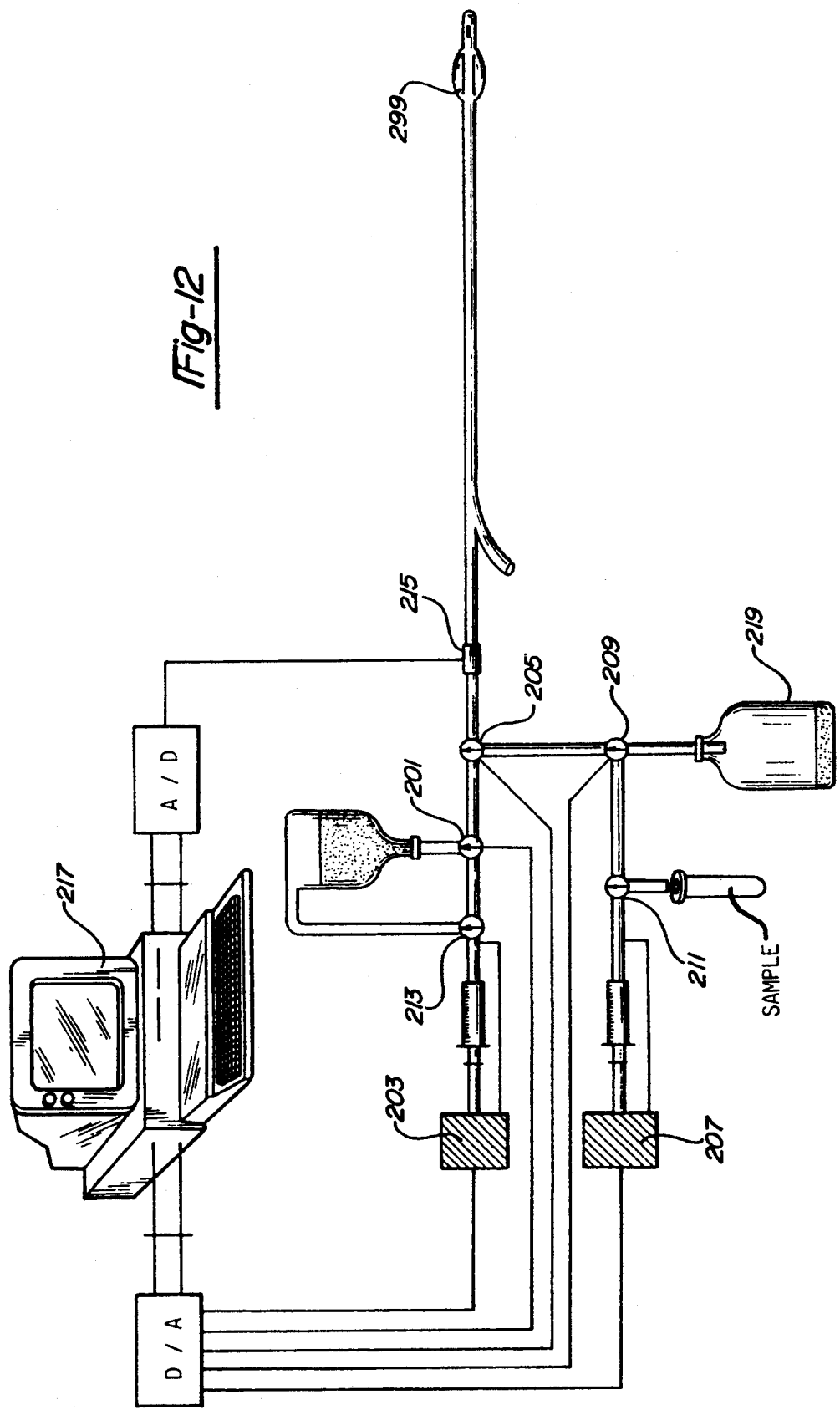
FIG. 12 illustrates one preferred example of the application of a tonometric catheter device, with remote sensing and recording apparatuses for monitoring and recording certain critical properties of interest.

In still another embodiment, conventional gas analyzers may be employed externally. A device such as that shown in FIG. 1 may be used in combination with a pump or aspiration means (not shown) for continuous or regular intermittent aspiration of a sample of the aspirating liquid or medium that is used to fill the sampling chamber 40. The sample removed by pump or aspiration means via attachment to the luer-lock 24 can be optionally designed so that the sample aspirated at each sampling interval can be brought in contact with an exterior, separate gas analyzing means or sensor (not shown) to determine the pH, pO$_2$, pCO$_2$ and/or the like, of the sample. Such automatic sampling can be conducted employing a system as shown in FIG. 12. In the assembly a sampling system employs a personal computer to conduct evaluations and analysis of the samples withdrawn from the tonometric catheter 299.

Pump 203 is loaded with the sampling or aspirating medium such as saline. Next, valve 201 is activated to withdraw a desired amount of the sampling fluid. The valve 201 is deactivated and pump 203 is used to enforce the sampling chamber of the tonometric catheter 299 using a calibrated amount or optionally a pressure transducer 215. The sampling fluid or medium is allowed to come to equilibrium with the wall of the organ or area of interest. Next the "dead space," i.e. the area of the lumen filled with the sampling fluid that is not in equilibrium, is removed by activating valve 205, activating pump 207, activating valve 209 and infusing pump 207; the waste 219 is discarded. A sample for analysis is then withdrawn by deactivating valve 209, activating pump 207 to then deliver the sampling to a gas analyzer such as an infrared or Raman gas analyzer (not shown) that provides data from the sample to the PC 217, and the evaluation is conducted as described herein.

The sample gas analyzer or a separate gas analyzer may be employed to determine the bicarbonate concentration in the arterial blood of the patient, as described above.

Figure 11:
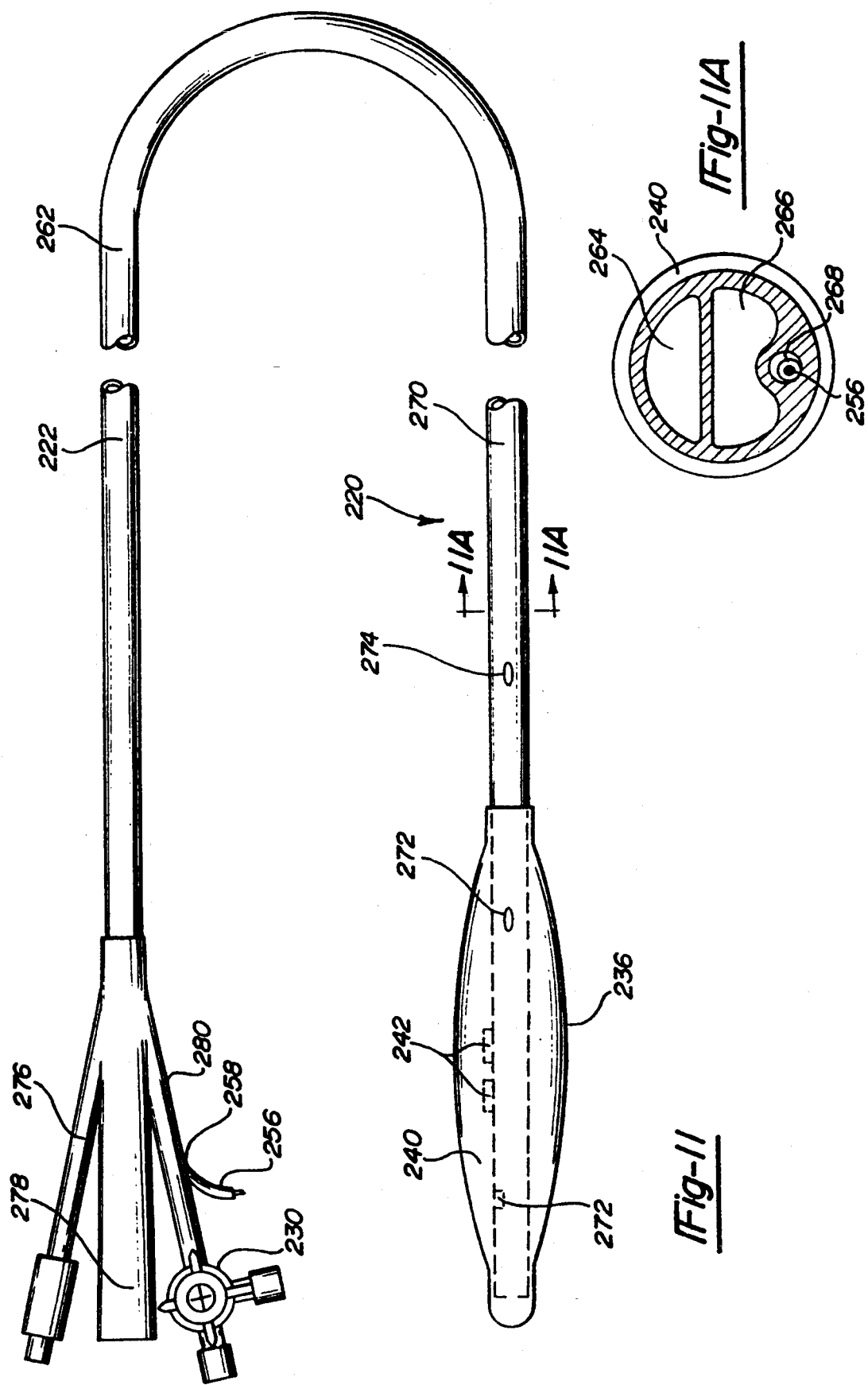
FIG. 11 is another embodiment of a tonometric catheter with a urinary catheter.

Another embodiment of the tonometric catheter is illustrated in FIGS. 11 and 11A. As illustrated, the tonometric catheter is appropriately configured to also serve as a urinary or ureteric catheter, either with or without suction, which optionally employs sensors. With reference to FIGS. 11 and 11A, the tonometric catheter 220 comprises a multipassage tubing 262 which defines three individual noncommunicating (between each other) passageways or lumens, an optional air or irrigation lumen 264, a drainage or suction lumen 266 and a tonometric catheter lumen 268. A tonometric catheter membrane, similar to that previously described, is attached at a distal location on tubing 262, allowing an intermediate portion of the tubing not extending beyond the end of membrane 236 to define the uretary or uretary catheter 270. Tubing 262 is provided with a plurality of perforations 272 which communicate between tonometric catheter lumen 268 and the sampling chamber 240 defined by membrane 236. If desired, one or more sensors 242 can be included in accordance with the above teachings, in which case a suitable conductor 256 may be routed through tonometric catheter lumen 268 to exit at sealed aperture 258.

The urinary catheter or ureteric catheter portion 270 is suitably provided with a plurality of openings 274 through which the bladder or ureters may be aspirated or irrigated.

At the opposite end of tubing 262 the tubing splits to form three separate connections. Air or irrigation lumen 264 optionally communicates with air lumen passageway 276, urinary lumen connects with suction or drainage lumen passageway 278 and tonometric catheter lumen 268 communicates with tonometric catheter lumen passageway 280. The tonometric catheter lumen passageway is fitted with three-way stopcock 230, similar in function and purpose to the three-way stopcock 30 described in connection with FIG. 1. If desired, a quick connect fitting 82 as seen in FIG. 4 may be used to couple the suction urinary passageway 278 with an aspiration source. As illustrated, the quick connect fitting preferably has angularly cut ends and a slightly enlarged midsection, making it easy to insert into the end of passageway 278 and also into the aspiration hose coupling (not shown). The enlarged midsection helps form a seal with the adjoining passageways. Preferably the quick connect fitting is fabricated of disposable plastic.

Yet another embodiment of the urinary catheter/tonometric catheter combination illustrated in FIGS. 11 and 11A may employ a multiple tonometric catheter embodiment employing a tubing having a plurality of passageways or lumens as shown in the cross-sectional view of FIG. 5A.

In another embodiment of the present invention, a tonometric catheter may be adopted to deliver a pharmaceutically-active agent, either for systemic, local or topical activity, or a combination thereof. For example, an additional lumen may be added such as that and for irrigation or aspiration, to deliver the active. For example, the irrigation/aspiration lumen 264 shown in FIG. 11 and 11A, may be used to deliver an active agent. In another embodiment, a portion of the device may be modified so as to provide sustained release of the active agent of interest.

Thus, for example, the problems of nosocomial infection associated with catheter insertion can be overcome by incorporating an antimicrobial into at least a portion of the polymeric material used to manufacture the tonometric catheter, or by coating at least a portion of the device with a sustained release composition, or by delivering the antimicrobial via the tonometric catheter. Such modifications are well known to those skilled in the art. See U.S. Pat. No. 4,677,143, incorporated herein by reference.

Classes of useful agents include antimicrobial agents, nonsteroidal anti-inflammatory agents, topical anesthetics, topical vasodilators, metabolic suppressants, and other agents that could be delivered for absorption at the sites of the tonometric catheter.

Figure 18:
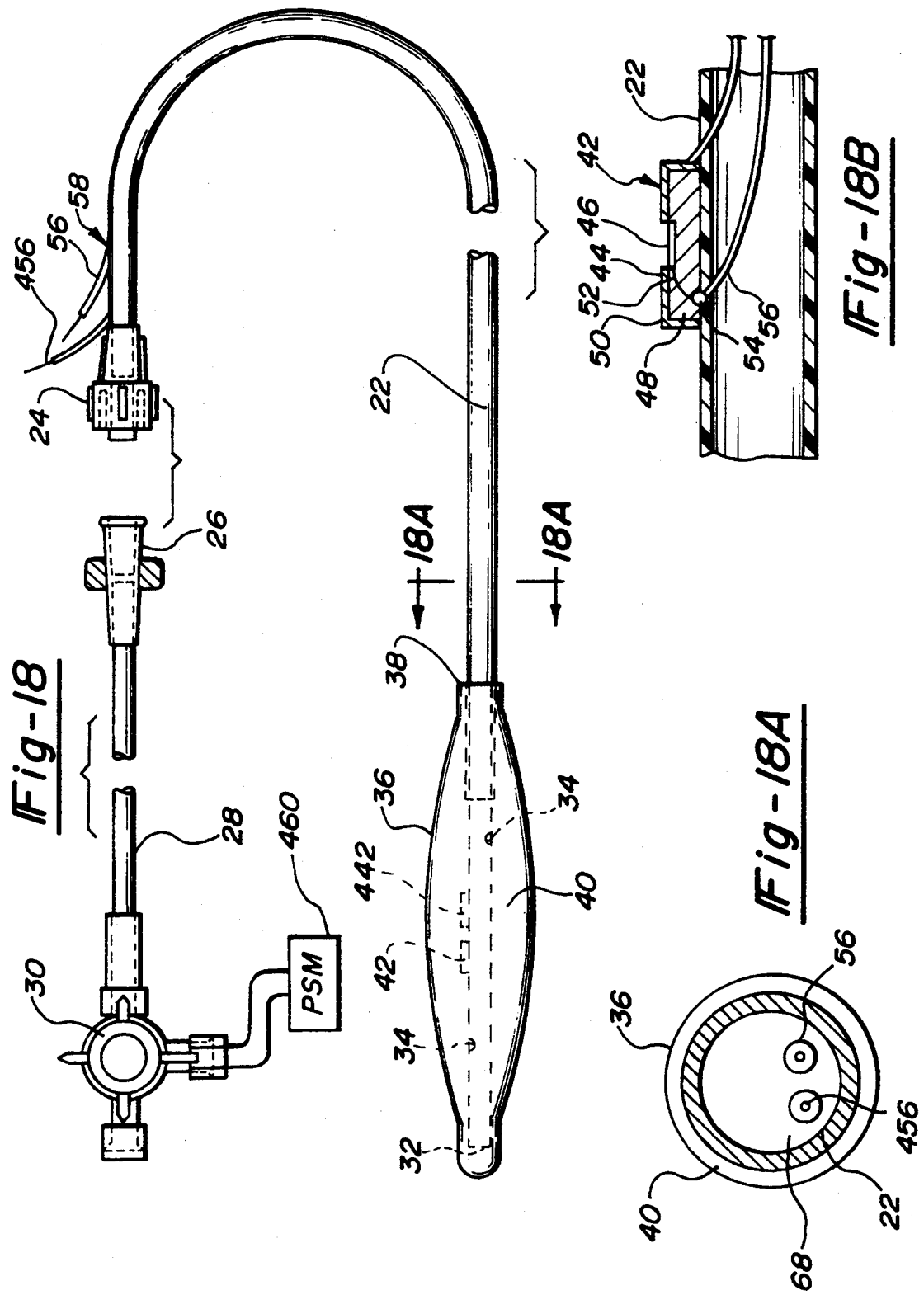
FIG. 18 illustrates a catheter with dual use pressure sensing and pHi sensing tonometric catheter.

In another embodiment as shown in FIG. 18, the catheter is appropriately configured to monitor both pHi and IAP. Pressure transmitting medium also serves as sampling fluid which may be charged into sampling chamber 40 so as to cause it to act as a pressure transmitting chamber. Once the system is charged, pressure sensing means 460 may be operably connected to stopcock 30 to monitor IAP.

Sensor 42 detects a property indicative of pH and/or temperature as discussed above. Electronic pressure transducer 442 can also be mounted on the catheter within the chamber 40 for sensing pressure and communicating its output via conductor 456 running through the lumen 68 of the catheter 22 as shown in 18A. The output of the pressure transducer 442 can be communicated via conductor 456 to a pressure display means such as an X-Y plotter or cathode ray tube.

In lieu of an internal pressure transducer 442 communicating via conductor 456, the chamber 40 can be charged with the sampling fluid which will also serve as the pressure transmitting medium. The pressure transmitting medium is in fluid communication with lumen 68 via opening 34 and can be monitored by a pressure sensing means such as a manometer or pressure transducer at a location external to the patient such as via one opening of the stopcock 30.

Where a single balloon is used as both a sampling chamber and as a pressure transmitting chamber, the membrane 236 should be selected to be permeable by the element which is to be sampled but relatively impermeable to the pressure transmitting medium.

In numerous clinical settings it is now common to monitor the carbon dioxide concentration of the arterial blood of patients, particularly those who are critically ill or under anesthesia; this measurement has been determined to bear a usually predictable relationship to pHi. One of the most common non-invasive techniques for measuring arterial $CO_2$ is doing so indirectly by measuring the $CO_2$ concentration of the last gas expired from a patient (so called "end tidal") during normal respiration. The arterial $CO_2$ concentration is then calculated by employing the known correlation between the end tidal $pCO_2$ and $pCO_2$ of the arterial blood.

It has been discovered in another aspect of the present invention that end tidal $CO_2$ (as well as the underlying correlation between end tidal $CO_2$ and the $pCO_2$ of arterial blood) may also be useful in making clinical determination of the condition of an organ of interest when the end tidal $CO_2$ is compared and contrasted with the $pCO_2$ of air aspirated from a tonometric catheter having a walled sampling chamber inserted into an organ of interest. These measurements having the added convenience of both being measurable by IR or Raman gas analyzers.

However, in order to fully appreciate this, a detailed understanding of the general tonometric method is useful. This background is helpful primarily for the skilled artisan to fully appreciate the relationship of moving from the general tonometric method (which employs $pCO_2$ associated with the wall of the organ of interest and the bicarbonate concentrations of arterial blood) to even more indirect but useful measurements.

In accordance with one preferred embodiment of the present invention, the condition of an organ of interest is determined in a patient in need of such determination when the $pCO_2$ associated with the wall of the organ of interest is sampled and compared to substantially contemporaneous arterial or venous $pCO_2$ values or, in a highly preferred embodiment, end tidal $pCO_2$ value(s); the $pCO_2$ of the wall of the organ may also be compared to: venous or arterial pH; mixed venous bicarbonate values; transcutaneous $pCO_2$; arterial oxygenation (saturation), and the like.

While not intending to be bound by theory, the following is offered to put these aspects and embodiments of the present inventions in proper context.

The assumptions upon which the indirect measurement of intramucosal pH (pHi) are based are valid in normally perfused tissues. In these circumstances, the indirect measurement of intramucosal pH is identical to that measured directly in the submucosal space with a microprobe.

The indirect measurement of pH falls in parallel with the pH made directly in the submucosal space when an intramucosal acidosis is induced by endotoxemia, low-flow or no-flow. In those circumstances in which the intramucosal acidosis in induced by endotoxin and flow to the gut is maintained at control levels the measurements are in close agreement ($r=0.945$). When induced by low-flow and especially no-flow the indirect measurements underestimate the severity of acidosis present in the submucosal space. The disparity between indirect and direct measurements observed in low-flow and no-flow states disappears when blood flow is reestablished and the pH is allowed to return towards normality. Inspection of the 20 minute values obtained in Antonsson et al's study reveals that the degree of dissociation observed between indirect and direct measurements is a linear function of the rate of change in intramucosal pH induced.

An additional primary assumption upon which the validity of the tonometric measurement of the adequacy of tissue oxygenation is that the bicarbonate concentration in tissue fluid is the same as that being delivered to it in arterial blood. It has been postulated that the dissociation between calculated and measured pH in low-flow and especially no-flow states may be due to a dissociation between arterial and interstitial bicarbonate induced by the buffering of metabolic acids by tissue bicarbonate.

The hypothesis does not account for the law of mass action which dictates that the fall in bicarbonate concentration induced by the addition of a fixed acid load to a "closed system" from which $CO_2$ cannot escape, such as the extracellular fluid compartment, is inhibited by the accumulation of $CO_2$. The addition of even large amounts of fixed acid to a "closed system" does not produce a significant reduction in bicarbonate concentration but does produce a significant rise in $pCO_2$. A fall in bicarbonate occurs only when venous blood enters the pulmonary circulation, an "open system" from which the $CO_2$ added to the venous blood by the buffering of the fixed acid load in the dysoxic tissue bed is able to escape. The fall in arterial bicarbonate thus induced causes the tissue bicarbonate to fall by equilibration with the lowered bicarbonate concentration in arterial blood returning to the tissue bed. The fall in arterial bicarbonate induced by the escape of $CO_2$ from the lungs cannot cause a reduction in tissue bicarbonate concentration in a no-flow state for it is unable to enter the tissue bed.

The tissue bicarbonate should be the same as that in arterial bicarbonate perfusing the tissue bed in all circumstances except perhaps very transiently after a sudden and large change in arterial bicarbonate induced by an intravenous bolus of bicarbonate or sudden change in pulmonary ventilation.

As a precaution, however, it is wise to wait until the arterial bicarbonate has been stable for some 10 to 15 or better yet 30 minutes before measuring the intramucosal pH after an intravenous bolus bicarbonate or sudden changes in ventilation regimes.

It is therefore suggested that the primary assumption upon which tonometric measurement of intramucosal pH is based, namely that the tissue bicarbonate is the same as that in arterial blood, is valid in many relevant clinical settings, including those in which the dissociation between measured and calculated intramucosal pH was greatest. The indirect measurement of intramucosal pH appears to be an accurate measure of the pH in interstitial fluid in the most superficial layers of the intestinal mucosa especially in those circumstances in which the measurement is of greatest value, namely patients who appear by all conventional criteria to be adequately resuscitated. The only circumstance in which the measurement might be inaccurate for an extended period is a no-flow state. In this circumstance, the indirect measurement is so abnormal that the presence of the intramucosal acidosis should not be missed even if there is a large discrepancy between actual and assumed measurements. Transient inaccuracies may be expected following an intravenous bolus of bicarbonate or sudden change in pulmonary ventilation.

Stoichiometric Analysis of Determinants of Tissue Acidosis

During aerobic metabolism the pH of tissue fluid is determined by the bicarbonate concentration in tissue fluid, the $CO_2$ released by oxidative phosphorylation, and the balance between ATP hydrolysis and resynthesis. In gastric glands the intracellular pH is the same as the extracellular pH in acidotic states. The pH of the extracellular fluid (ECF) is determined by the amount of metabolic acid present and the ability of the ECF to buffer the acid. The $pCO_2$ attained following the buffering of a volatile ($H_2CO_3$ from oxidative phosphorylation) or fixed acid load (protons from ATP hydrolysis) in a closed system, (FIG. 5) such as the ECF, may be calculated in the manner described by Gattinoni and Feriani.

In normoxic tissues 6 mmol of $CO_2$ are produced for every mmol of glucose consumed in the generation of 38 mmol ATP. 13.5% of a volatile carbonic acid load added to ECF remains after being buffered by proteins and determines the $pCO_2$ present in the ECF. Assuming that the bicarbonate concentration in ECF is 25 mEq/l the metabolism of one mM glucose is 27 mmHg ($6\times0.135/0.03$). In normoxic and resting healthy subjects with a tissue bicarbonate of 25 mEq/l the $pCO_2$, determined tonometrically, is 40 mmHg and the intramucosal pH 7.40. If it is assumed that the protons released by ATP hydrolysis are exactly balanced by the protons consumed by ATP resynthesis in oxidative phosphorylation then the aerobic metabolism of 1.48 mM glucose is required to generate the volatile carbonic acid necessary to attain the $pCO_2$ of 40 mmHg ($27\times1.48=40$ mmHg) and pH of 7.40 found in nontoxic ECF when the tissue bicarbonate concentration is 25 mEq/l.

The $pCO_2$ attained from the buffering of the volatile acids released into normoxic ECF in a tissue bed should increase as the metabolic rate increases, the increased demand for oxygen in the absence of replenishment by flowing blood being met exclusively by an increase in oxygen extraction ratio. A rise in metabolic rate of the magnitude seen in an exercising athlete, which may be as great as 900%, can be expected to cause a rise in equilibrium $pCO_2$ and hence fall in intramucosal pH in normoxic tissues. The magnitude of the fall in pH induced by the rise in $pCO_2$ is offset by the rise in tissue bicarbonate also induced by the buffering of carbonic acid (a volatile acid). The rise in metabolic rate observed in the critically ill is a fraction of that seen in an exercising athlete. Furthermore the oxygen extraction ratio is unchanged and more often decreased in septic patients who exhibit the highest metabolic rate in the critically ill. In any event, the increased metabolic demand for oxygen in the critically ill, especially in those who are septic, is primarily met by an increase in oxygen delivery, oxygen delivery being "demand-dependent" in these circumstances. The $pCO_2$ attained by the buffering of the volatile acid load generated in normoxic ECF should not, therefore, be significantly influenced by changes in metabolic rate of the order encountered in the critically ill.

Aerobic glycolysis and associated generation of $CO_2$ by oxidative phosphorylation decreases in dysoxic states as the availability of oxygen relative to demand decreases. Thus the fall in tissue pH in severely dysoxic states is due almost exclusively to the protons released by adenine nucleotide hydrolysis and their interaction with the body buffers.

If it is assumed that the intramucosal $pCO_2$ and pH are solely determined by the amount of volatile and fixed metabolic acid being buffered in the ECF at the time, the intramucosal pH can be expected to remain constant as oxygen delivery is reduced with or without a reduction in blood flow until the point at which supply-dependency or dysoxia develops. Below this point the $pCO_2$ in ECF should rise and the intramucosal pH fall as the contributions by aerobic metabolism to volatile acid decreases and by anaerobic metabolism to proton release increases with further reductions in oxygen delivery.

Actual Intramucosal pH

The buffering of the protons by tissue bicarbonate in dysoxic states causes the $pCO_2$ to rise. As the bicarbonate concentrations in a "closed system" such as the ECF, is not significantly reduced by the addition of a fixed acid load, the fall in pH must be inversely related to the rise in log $pCO_2$ at any given concentration of tissue bicarbonate. The constant bicarbonate line at 25 mEq/1 on a pH-log $pCO_2$ diagram will show that the $pCO_2$ in normoxic ECF at a point A to be 40 mmHg and the pH to be 7.40. The bicarbonate line moves to the right as the equilibrium $pCO_2$ rises above 40 mmHg to a point B in dysoxic states and the tissue pH falls below 7.40. The pH in the dysoxic state may be determined by extrapolation from the $pCO_2$ intercept on the constant bicarbonate line at 25 mEq/1.

The fall in pH induced by dysoxia alone in a tissue with a known bicarbonate concentration may be computed from the difference between the pH in the normoxic and dysoxic states determined from the same constant bicarbonate line (pH-gap), log of the ratio $pCO_{2t}/pCO_{2a}$ (B−A) or their antilog equivalents ($pCO_2$-gap and H+-gap). These determinations of the magnitude in fall in pH induced by dysoxia are all dependent upon the assumption that the bicarbonate concentration in the dysoxic ECF is the same as that present in normoxic ECF. If it is assumed that the $pCO_2$ in normoxic ECF is the same as that in arterial blood ($pCO_{2a}$) and the tissue $pCO_2$ in dysoxic ECF is the same as the intramucosal $pCO_2$ measured from the lumen of the gut with a walled sampling chamber tonometer ($pCO_{2t}$) then the actual pH in dysoxic ECF may be calculated from the following formula (with $pH_a$=pH of arterial blood):

Actual intramucosal $pH = pH_a − (\log pCO_{2t} − \log pCO_{2a}) = pH_a − \log pCO_{2t}/pCO_{2a}$ and displayed in a perceptible form, such as human readable or audible form, or machine readable form.

Standard Intramucosal pH

The normoxic isobar shifts in one direction with a metabolic acidosis and to the other direction with a metabolic alkalosis, but the dysoxic component is still indicated by the difference between the dysoxic and normoxic isobars at the same bicarbonate concentration. This confounding influence of the presence of a metabolic acidosis or alkalosis in the determination of the degree of dysoxia present may be eliminated by standardizing the pHi to that present if the bicarbonate concentration were 25 mEq/1:

Standard intramucosal $pH = 7.40 − \log pCO_{2t}/pCO_{2a}$

The standard intramucosal pH is easily interpreted by clinical staff who all know that 7.40 is a normal pH. It is the same as the actual pH in patients whose arterial pH is normal but differs from the actual pH with systemic disturbances in acid-base balance. As indicated above, the "pH-gap", log of the ratio $pCO_{2t}/pCO_{2a}$, and their antilog equivalents may also be used as indices of the degree of dysoxia present independently of changes in tissue bicarbonate provided that the bicarbonate concentration in the tissue is the same as that in arterial blood and remains constant. The $pCO_{2t}$ alone does not provide a reliable measure of either the actual tissue pH or the degree of dysoxia present for interpretation of the measurement is confounded by alterations in arterial bicarbonate.

This analysis suggests that the actual measurement of intramucosal pH may be capable of detecting the presence of dysoxia whenever the delivery of oxygen fails to meet more than about 20% of the tissue's needs especially if the arterial pH is normal. The analysis further suggests that the use of standard intramucosal pH in addition to actual intramucosal pH may improve the sensitivity of measures of the degree of dysoxia present.

Clinical Implications

The indirect measurement of intramucosal pH (pHi) provides an accurate diagnostic test for the presence of macroscopic and clinical evidence of gastric, small intestinal and large intestinal ischemia in patients. The sensitivity of the intramucosal pH as a diagnostic test for gastric ischemia in man is reported to be 95% and the specificity 100%. For severe ischemic colitis after abdominal aortic surgery the sensitivity is reported to be 100% and the specificity 87%. Of particular relevance to patients who are critically ill is the inability of those with an intramucosal acidosis to secrete acid in response to pentagastrin. Those patients who have a normal gastric intramucosal pH secrete acid in response to this stimulus. It has been suggested that the inability to secrete acid in patients with an intramucosal acidosis may be due to an energy deficit secondary to a dysoxic state. An energy deficit is a known cause of stress ulceration in animals and an impairment of gastric mucosal oxygenation the likely cause of stress ulceration in patients.

The gastric intramucosal pH, measured following the administration of an $H_2$ receptor antagonist to avoid confounding influence of the back diffusion of acid and/or $CO_2$, is inversely related to the hepatic venous lactate concentrations in patients having cardiac surgery (r=−0.71) and correlates closely with this and other indices of splanchnic tissue oxygenation (r=0.92).

The gastric intramucosal pH provides, therefore, an index of the adequacy of splanchnic tissue oxygenation.

The gastric intramucosal pH correlates very well and inversely with systemic blood lactate when it is abnormally elevated. In many circumstances, however, blood lactate is normal when the intramucosal pH is low and no correlation between the variables can be demonstrated. Indeed a fall in gastric intramucosal pH may precede a rise in blood lactate in a deteriorating patient by many hours or even days. Changes in actual pH influence the pH dependent enzymes regulating carrier mediated afflux of lactate from muscle and the pH dependent enzyme phosphofructokinase which regulates the rate of anaerobic glycolysis. In addition blood lactate is the net effect of both production by anaerobic glycolysis and consumption by tissues such as the myocardium. The overall correlation between the two variables is thus rather poor ($r = -0.40$) but nevertheless statistically significant ($p = 0.026$). Thus in addition to providing indices of gastric mucosal and splanchnic tissue oxygenation the indirect measurement of gastric intramucosal pH provides an index of the adequacy of global tissue oxygenation.

The indirect measurement of intramucosal provides a measure of the adequacy of tissue oxygenation in the most superficial layer of the mucosa, a region of the gut rendered relatively hypoxic by the counter current exchange system within the mucosal vasculature and hence especially sensitive to alterations in the adequacy of tissue oxygenation. It also provides a measure of the adequacy of tissue oxygenation in a region of the body that is among the first to develop an inadequacy of tissue oxygenation or dysoxia in shock and the last to be restored to normality with resuscitation. Splanchnic vasculature is selectively constricted by the endogenous vasoconstrictors released in shock. For these reasons a fall in intramucosal pH may occurs hours to days in advance of any other conventional evidence of an inadequacy of tissue oxygenation, most specifically arterial acidosis, elevation in blood lactate, hypotension and oliguria.

It is concluded that the indirect measurement of gastric intramucosal pH provides a sensitive measure of the adequacy of splanchnic and even global tissue oxygenation in patients in addition to providing an index of the adequacy of superficial gastric mucosal oxygenation.

Correlations With Acid-base Balance and Clinical Events

The indirect measurement of gastric intramucosal pH may correlate very closely with the arterial pH ($r = 0.67$) and other systemic indices of a disturbance in acid-base balance such as arterial bicarbonate ($r = 0.50$), the base deficit in extracellular fluid ($r = 0.60$) and base deficit in blood ($r = 0.63$). This is consistent with the deduction that gastric intramucosal pH provides an index of the balance between the protons released by ATP hydrolysis and consumed in the resynthesis of ATP by oxidative phosphorylation. As with global measurements of blood lactate changes in systemic acid-base balance provide a very dampened signal of disturbances in the adequacy of tissue oxygenation. A fall in intramucosal pH will often precede a fall in arterial pH by hours or even days.

The predictive value of measurements of gastric intramucosal pH for outcome are superior to those of the systemic measures of acid-base balance. Maynard et al, for example, compared the predictive value of measurement of gastric intramucosal pH with those of arterial pH and base excess for death in ICU patients. The likelihood ratio for pHi was 2.32, for arterial pH 1.52 and base excess 1.47. Logistic regression showed only pHi to independently predict outcome. In Boyd et al's study, the gastric intramucosal pH was likewise of better predictive value for outcome than base excess. Clinical experience has shown that changes in gastric intramucosal pH correlate far better with the passage of clinical events than either the arterial pH or base excess. Indeed abnormalities in these systemic measures of acid-base imbalance will often occur only as the intramucosal acidosis is being reversed and the patient's condition is improving.

Reperfusion after the low-flow and particularly no-flow states induced in Antonsson et al's validation study in pigs caused the intramucosal pH to rise and the arterial bicarbonate to fall. Similarly in patients the reversal of a severe intramucosal acidosis may be accompanied by a fall in arterial pH and base excess at abnormally low levels. These observations are consistent with the consequences described above of reestablishing perfusion in a dysoxic tissue bed in patients. The $pCO_2$ in the venous effluent leaving the dysoxic tissue bed is elevated but the bicarbonate concentration is not significantly reduced by the buffering of the fixed acid in the tissue bed. The bicarbonate is only reduced by the loss of $CO_2$ during the passage of the venous effluent through the pulmonary circulation (an open system). As dissociation between the direction of change in the intramucosal and systemic pH is to be expected after flow is reestablished through a dysoxic tissue bed.

Intramucosal pH as a Therapeutic Target

"Gut-directed" and "pHi-directed" therapies may improve outcome. These therapies use a normal pHi or pHi greater than 7.35 as an additional therapeutic goal in the resuscitation of patients. This pH was chosen to ensure the pH was maintained well within the normal limits reported for normal subjects. The normal limits may, however, differ from institution to institution with the use of saline and different blood gas analyzers, a problem solved by the air sampling medium/IR $pCO_2$ analysis embodiments of the instant invention. It is furthermore possible that an end-point other than 7.35 might be more appropriate. Values such as 7.25; 7.30; 7.35; 7.37 etc. may also be useful.

While it is clearly desirable to maintain a normoxic state by maintaining the standard pHi at 7.40, it is not necessarily desirable to maintain the actual pHi at 7.40. There is a considerable body of evidence indicating that mild degrees of cellular acidosis protect cells in anoxia and ischemia possibly by limiting the activity of the autolytic enzymes responsible for cell injury and death. A cellular acidosis may in addition facilitate carrier-medicated afflux of lactate from cells and bring the intracellular pH to an optimal range for anaerobic glycolysis during anaerobic metabolism. Furthermore the addition of bicarbonate to the extracellular environment attenuates the fall in intracellular pH during ATP depletion and accelerates cell death. The presence of an actual intramucosal acidosis may, therefore, be desirable and efforts to correct a metabolic acidosis with bicarbonate potentially harmful. Indeed the practice of correcting a metabolic acidosis induced by a cardiac arrest by the administration of bicarbonate is no longer recommended.

It is concluded that acid-base balance is intimately related to the adequacy of tissue oxygenation in so far as it relates to the balance between the protons released by ATP hydrolysis and consumed by ATP synthesis from oxidative phosphorylation. The tissue pH is determined by the $pCO_2$ attained following and buffering of the metabolic acid released into the ECF and the bicarbonate concentration in ECF at the time—the "buffer hypothesis". The intramucosal pH is related to blood flow only in so far as it relates to the adequacy of tissue oxygenation. The assumption that tissue bicarbonate is the same as that in arterial bicarbonate is only valid in the absence of the generation of an alkaline tide and associated secretion of acid. The indirect measurement of actual gastric intramucosal pH is the sump of the effects of several determinants of an intramucosal acidosis. It is relevant to activity of pH-dependent enzymes especially as they might relate to cellular injury in dysoxic states. By eliminating the confounding effects of disturbances in systemic acid-base balance the standard gastric intramucosal pH provides a measure of the acidosis attributable to an imbalance between ATP hydrolysis and resynthesis, or degree of dysoxia present. Systemic measures of acid-base balance may be dissociated from the adequacy of tissue oxygenation upon reperfusion of a dysoxic tissue bed and correlate poorly with clinical events relative to the measurement of gastric intramucosal pH.

In light of all the above, it will be appreciated that one series of embodiments of the present methods relate to the use of arterial carbon dioxide concentrations (measured directly or indirectly, preferably as an end tidal carbon dioxide value) as a predictive indicator of the pH of the most superficial layer of the mucosa of the wall of an internal solid organ, particularly the gut. In recognizing that $$pHi = pH_a + \log \frac{pCO_{2a}}{pCO_{2t}}$$

and that $pCO_{2a}$ is approximately equal to $pCO_{2\text{-end tidal}}$, thus $$pHi = pH_a + \log \frac{pCO_{2\text{-end tidal}}}{pCO_{2t}}$$

Either or both of these may be employed.

In accordance with the practice of the methods of the present invention, the $pCO_2$ of the wall of the organ is determined. This is preferably done by inserting a tonometric catheter with a walled sampling chamber into or adjacent the organ of interest. The sampling chamber is filled with a gaseous or liquid sampling medium such as air or saline. The sampling medium is allowed to come to equilibrium (equilibrate) with the area so that the $pCO_2$ concentration of the sampling medium reflects the $pCO_2$ of the superficial layer of the mucosa of the organ of interest. The $pCO_2$ concentration of the sampling medium is determined, giving $pCO_{2t}$.

In conjunction with the determination of the $pCO_2$ of the mucosa, the carbon dioxide concentration in arterial ($pCO_{2a}$) or venous blood is determined directly or indirectly. (A highly preferred indirect measure is end tidal $pCO_2$, or $pCO_{2\text{-end tidal}}$). The two values (e.g., $pCO_{2a}$ and $pCO_{2t}$) are then subjected to a nomogram, such as those described in equations above, to determine for example, a pHi value or pH gap.

In a highly preferred embodiment, the sampling medium for the walled sampling chamber is air. The air is aspirated to an IR or Raman spectrometer. In combination, the measurement of end tidal $pCO_2$ is employed as a substitute for the arterial $pCO_2(a)$. The end tidal respiratory air is likewise aspirated to an IR or Raman spectrometer. Both gas analyzing devices are controlled by a microcomputer, which also effects the selected nomogram or nomograms which compare the $pCO_2$ of the wall of the organ (gut) with the end tidal $pCO_2$ value. The gas analyzing devices may operate on a single channel, or via multiple channels.

Additional detection techniques may be performed on the air aspirated from the patient, either via respiration or from the tonometric walled sampling chamber. For example, IR or Raman analyses may be performed to determine the level of anesthetic gases, such as $N_2O$. The results of the nomogram are displayed on a monitor (not shown) in human or machine readable form.

In a highly preferred embodiment, the operation of one example of an infrared gas analyzer is controlled by a microcomputer. The microcomputer itself is not, by itself, part of the present invention. For this reason and because one skilled in the relevant arts could routinely program a general purpose computer to follow the routines required for this application, the microcomputer will not be described in detail herein. (See the U.S. patents incorporated herein by reference.)

Figure 13:
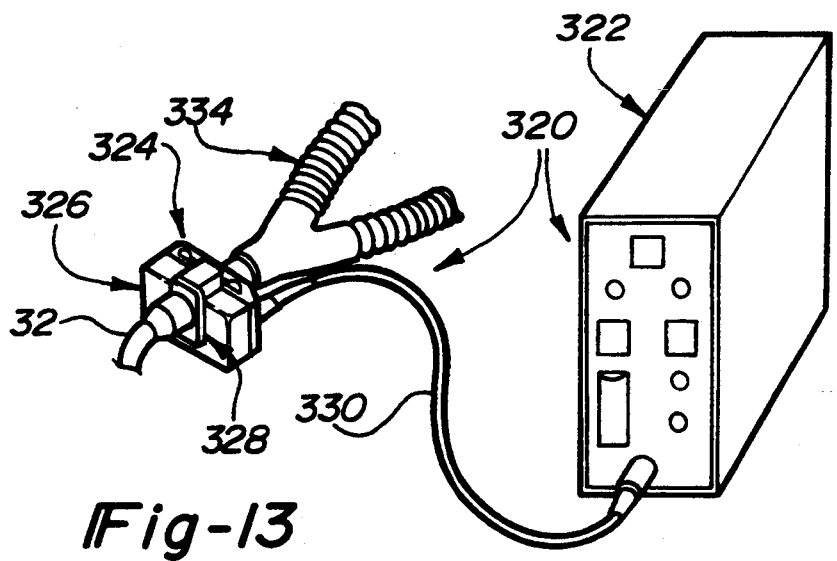
FIG. 13 is a diagrammatic representation of an exemplary non-dispersive infrared gas analyzer system usable in the present invention.

Referring now to FIG. 13, a gas analyzer or detector 320 is shown in accord with the principles of the present invention. Analyzer 320 is specifically designed to monitor the concentration of carbon dioxide in the exhalations of a medical patient—e.g., a patient being ventilated during a surgical procedure.

The major components of the infrared gas analyzer 320 are a powered unit 322 and a sensor assembly 324 of a transducer head 326 and an airway adapter 328. The transducer head 326 is connected to the unit 322 of the gas analyzer 320 by a conventional electrical cable 330.

In the application of the invention depicted in FIG. 13, the gas analyzer 320 is employed to measure fluid parameters of interest, similar to the apparatuses shown and discussed above, except that a gaseous sampling medium, such as air, is conveyed, either manually or automatically, as shown above, and analyzed by the infrared sensor assembly 324, where the sampling medium is conveyed to the assembly 324 via one of the above described tonometric catheter devices. This information can be effectively employed by medical personnel to monitor the condition of a patient's internal organ more accurately and more quickly than before.

FIG. 13 depicts an in-stream type of infrared gas analyzer, shown merely for purposes of illustration, but one skilled in the art will appreciate that the same principles apply to the use of a side-stream type IR gas analyzer.

Figure 14:
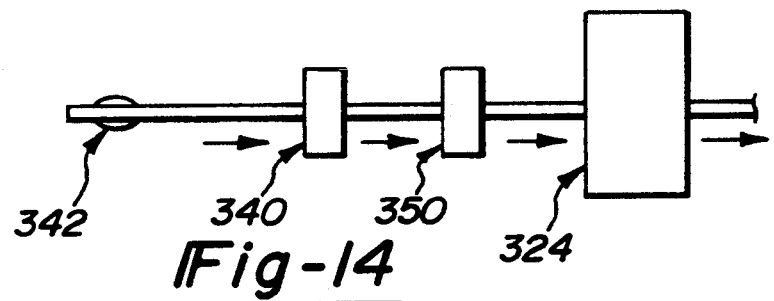
FIG. 14 is a schematic representation of an alternate variation of a tonometric catheter usable in the invention.

FIG. 14 schematically illustrates a biological filter (bio-filter) apparatus 340 being employed in-line, between an exemplary tonometric catheter apparatus 342 and the above-discussed exemplary infrared sensor assembly 324. The bio-filter 340 can be any of a number of biological filters known to those skilled in the art and is especially useful to allow side-stream systems to allow sample return or in-stream infrared gas analyzer apparatuses to be used in multi-patient applications.

Due to the sensitivity of the current commercial infra red sensors or detectors to moisture content, and due to the high moisture content of air sampling-medium based $pCO_2$ samples coming from both in vivo tonometric walled sampling chamber and end tidal samples, a moisture filter or other dehumidifying means is preferably employed.

For example, air-based $pCO_2$ sample can be passed through dehumidification tubing, such as Nafion tubing.

Other methods of eliminating moisture problems include employing a heat sink around part or all of the IR optical path, particularly the lens window where the IR source passes light. Yet another means includes employing a barrier or filter which is selectively permeable to water vapor (moisture) and/or the gases of interest, particularly $pCO_2$.

It should therefore also be noted that the filter 340 can also optionally include a dehumidifying means, e.g., a water vapor filter or removal medium, either alone or in addition to the biological filter, for allowing any water vapor in the sampling medium or the sampling chamber to disperse in the environment by delivering the mixture thereof past a water-vapor-permeable wall or medium.

FIG. 14 also schematically illustrates the addition of a gaseous sampling medium pressure sensor and/or regulator 350 (optional) for measuring the pressure of a gas sampling medium, such as air, for example, and/or for regulating such pressure to be substantially at some predetermined pressure level, such as atmospheric pressure, for example, at which the IR gas analyzer is designed to operate and give accurate, reliable results.

It will be appreciated that Raman spectrometers (gas analyzers) offer advantages over IR in the present invention, including the fact that such dehumidifying means need not be employed. Additionally, the use of this combination (a tonometric catheter plus a Raman spectrometer) would allow the measurement of oxygen gas; nitrogen gas; water; $N_2O$ and other anesthetic agents such as halothane, enflurane, isoflurane, serroflurane, and desflyrane, all of which exhibit Raman scattering. Raman devices not only measure $pCO_2$ more accurately, but can measure $N_2$, $O_2$ and $H_2O$ directly. This may reduce the potential error associated with certain IR techniques, especially where other material ($N_2O$; $O_2$; $H_2O$) may effect the $pCO_2$ IR measurement. It also would allow detection of air leaks.

Another important advantage would be the ability to employ a fiberoptic probe within the sampling chamber 40 of the tonometric catheter.

Significant deviations from this "design" gaseous sample pressure level can result in inaccurate readings due to density changes resulting from the gas being over-pressurized or under-pressurized.

Figure 15:
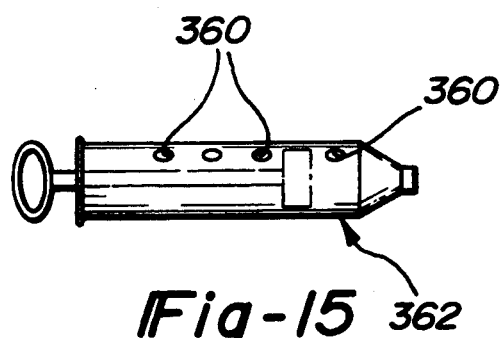
FIG. 15 is a diagrammatic representation of a manual syringe, modified to provide for sample pressure equalization usable in the present invention.

In a manual system, wherein a syringe is used to draw the gaseous sample into the sensor assembly, it has been found to be useful to provide one or more holes 360 in the syringe body 362 shown in FIG. 15 in order to allow for pressure regulation and equalization with the atmosphere. Alternatively, a pressure-difference caused by a pump, with or without a pressure regulation or connection device, as needed, can be employed. In addition, as is clear from the foregoing discussion, the system can use a single-tube catheter device or a dual-tube version, wherein one tube delivers the sampling medium to the sampling chamber and the other is used to extract it for measurement.

Clinical Example

In the following clinical study, approval was received by the appropriate hospital ethics committee and informed consent was obtained from the patients. Recordings were performed in ten patients undergoing laparoscopic cholecystectomy at Liverpool Hospital, Sidney Australia. All patients underwent a general anesthetic with muscle relaxation and artificial ventilation. The patients were placed supine upon the operating table. All patients had nasogastric insertions of a nasogastric tube with a pressure transmitting chamber attached. The balloon on the nasogastric tube was one usually employed for tonometry, namely indirectly measuring intramural pH, i.e. a TRIP TGS catheter from Tonometrics, Inc., Worcester, Mass. U.S.A. The intragastric position of the tonometer was confirmed by aspiration of gastric fluids, auscultation of air insufflation of the stomach, and confirmation of a rise of IAP following external epigastric pressure. None of the patients had intraabdominal adhesions. The stomach was visualized at laparoscopy to confirm its intra-abdominal position.

The pressure volume curve of the gastric balloon at 37° centigrade confirms that inflation of up to 3.0 ml of air allowed the balloon to reflect changes in IAP. Each balloon was individually checked prior to insertion. The balloon on the nasogastric tube was completely emptied prior to injection of 2.5 ml of air. Particular attention was paid to make sure that the stomach was in a period of quiescent motor activity with no evidence of the phase II or phase III of the migrating motor complex Vantrappen G. *The migrating myoelectric complex*. In Motility of the digestive tract. Weinbeck M, New York, Raven Press 1982;157–167.

A size 16 Foley catheter was inserted into the bladder. A T-piece bladder pressure attachment was attached to the in-dwelling catheter and a primed pressure transducer was connected to the system. The pressure transducer connected to the urinary catheter was placed at the same level in the mid-axillary line as a transducer which was primed and connected to the nasogastric tube. 50 ml of normal saline was inserted into the bladder via a three way stopcock. The urinary catheter was clamped.

Simultaneous IAP recordings were obtained by means of an intragastric balloon catheter and urinary catheter transduced to a Datex AS3 three channel recorder. After zeroing the transducer, the pressures from both the stomach and bladder were recorded simultaneously with a two chart recorder. The volume of intraperitoneal gas was recorded. Insufflation pressure was limited to 20 millimeters Hg. The $CO_2$ was insufflated at a rate of two liters per minute. The nasogastric and urinary catheters were removed at the end of the procedure.

Statistical analysis was carried out using SAS version 6.04. Pearson product moment correlations coefficients and Spearman rank coefficients were used to assess the relationships between the intravesical and gastric pressures in each patient. Adjustments for age and body mass index were not attempted. The mean 95% confidence interval of the 9 slopes were calculated.

There were 8 females and 2 males aged 43 plus or minus 15 years. The mean body mass index was 30 plus or minus 5. Insufflation of the abdominal cavity was achieved with carbon dioxide to a preset pressure of 20 mmHg as regulated by the insufflator (Wisap). Mean volume of gas insufflated was 8.8 plus or minus 4.3 liters. Baseline pressures were 0–2 mmHg in all patients rising to a mean maximum pressure of 14 plus or minus 4 mmHg range 8–20 mmHg.

Figure 20:
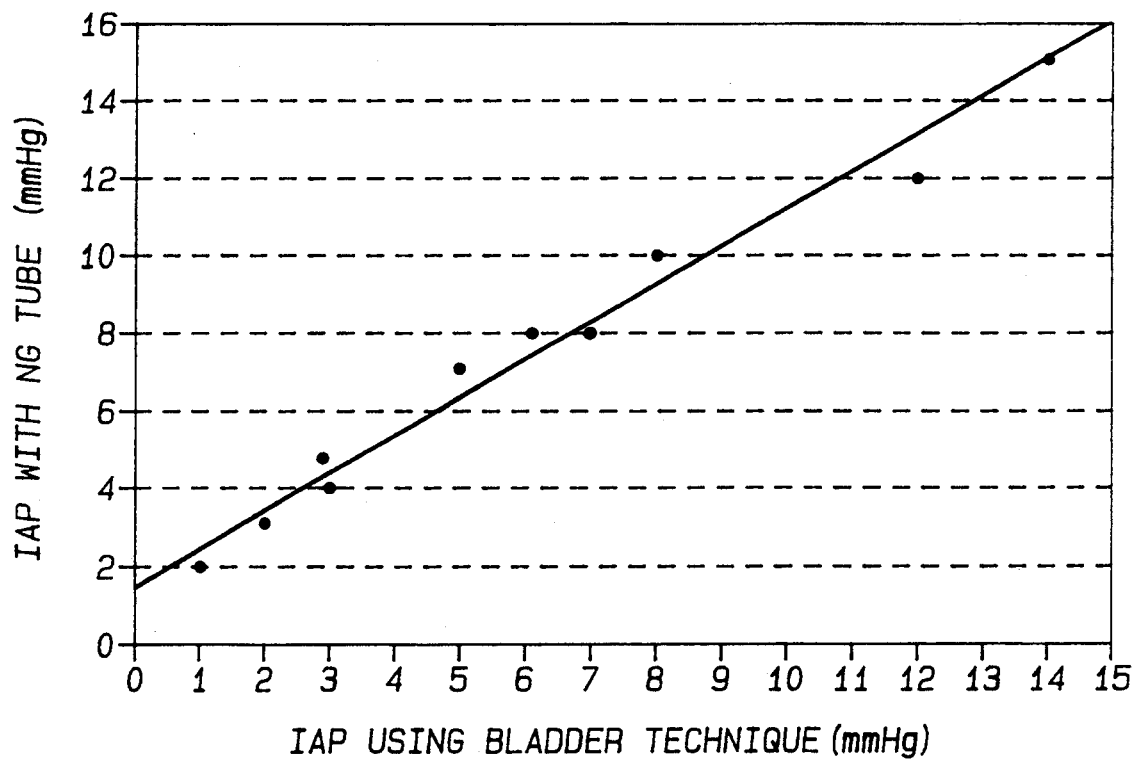
FIG. 20 is a chart showing the relationship of intravesical and gastric pressure in a subject patient.

Simultaneous IAP recordings were obtained by means of the intra-gastric balloon and urinary catheter transduced to a Datex AS3 three channel recorder. The pressure volume response was variable, due to the different peritoneal capacity of individual patients. Transduced pressures had a rapid response time facilitating recording of changes during insufflation. The mean insufflation time to these pressures was 4.7 plus or minus 1.9 minutes. There was a very strong correlation for all pressures up to 17 mmHg. Individual correlations coefficients range from 0.90 to 0.99 (p less than 0.01). FIG. 20 shows the relationship between intravesical and gastric pressures in one of the patients. The results of one patient were excluded due to protocol violation as the balloon required the installation of 2.5 ml to allow it to record pressures, however, the correlation for this patient was 0.95.

IAP measured by the gastric technique can be predicted by the following equation:

$$IAP = 0.17 + 1.05 \times \text{intravesical pressure.}$$

The 95% confidence intervals for the intercept were −1.22 to 1.56, and for the slope 0.86 to 1.24.

Accordingly, while several preferred embodiments of the invention have been disclosed, it will be appreciated that principles of the invention, as set forth in the following claims, are applicable to other embodiments.

What is claimed is:

1. A tonometric catheter apparatus for measuring the internal pressure of a human or other mammal comprising:
   (a) an elongated tonometric catheter tube having at least one lumen extending longitudinally therethrough;
   (b) at least one walled pressure transmitting chamber on said catheter tube in pressure transmitting communication with the interior of said lumen, said walled pressure transmitting chamber generally surrounding a portion of said catheter tube and being sealingly interconnected therewith, being composed of a wall material being substantially impermeable to liquid fluids or wherein at least a portion of the wall of said chamber being composed of a wall material that is freely and selectively permeable to one or more liquid fluids or gaseous fluids of interest, said wall material being substantially impermeable to other interfering liquid fluids or gaseous fluids, and wherein said pressure transmitting chamber forms an interior space with said catheter tube in order to allow the transmission of change in pressure through said pressure transmitting chamber to the interior of said lumen via a pressure transmitting medium; and
   (c) pressure sensor means for measuring the pressure of said pressure transmitting medium.

2. An apparatus according to claim 1 wherein said walled pressure transmitting chamber is defined by a balloon member generally surrounding a portion of said catheter tube and sealingly interconnected therewith.

3. The apparatus according to claim 1 wherein said pressure transmitting chamber is in fluid continuous communication with said lumen.

4. An apparatus according to claim 1 wherein said pressure transmitting medium is air.

5. An apparatus according to claim 1 wherein said pressure transmitting medium further comprises a saline solution.

6. An apparatus according to claim 1 wherein said pressure sensor means further comprises a manometer.

7. An apparatus according to claim 1 wherein said pressure sensor means further comprises a pressure transducer.

8. An apparatus according to claim 1 wherein said pressure transmitting medium further comprises a buffered solution.

9. An apparatus according to claim 1 wherein the wall material is silicone.

10. A tonometric catheter apparatus for measuring a liquid fluid or gaseous fluid property indicative of the internal pressure of an internal cavity of a human or other mammal in vivo comprising:
    (a) an elongated tonometric catheter tube having at least one lumen extending longitudinally therethrough;
    (b) at least one walled pressure transmitting chamber on said catheter tube in pressure transmitting communication with the interior of said lumen, said walled pressure transmitting chamber being defined by a balloon member generally surrounding a portion of said catheter tube and being sealingly interconnected therewith, wherein at least a portion of the wall of said chamber being composed of a wall material that is freely and selectively permeable to one or more liquid fluids or gaseous fluids of interest, said wall material being substantially impermeable to other interfering liquid fluids or gaseous fluids, and wherein said balloon member is capable of being inflated for forming a pressure sensing diaphragm for acting upon pressure transmitting medium within said walled pressure sensing chamber; and
    (c) pressure sensor means for sensing the pressure of said pressure transmitting medium.

11. An apparatus according to claim 10 wherein said pressure sensor means includes an interface means for converting an output of said pressure sensor means into a human readable format.

12. An apparatus according to claim 10 wherein said pressure sensing means further comprises a pressure transducer.

13. An apparatus according to claim 10 wherein said pressure sensing means further comprises a manometer.

14. An apparatus according to claim 12 wherein said pressure transducer is mounted within said pressure transmitting chamber.

15. An apparatus according to claim 11 wherein said pressure transmitting medium is air.

16. An apparatus according to claim 11 wherein said pressure transmitting medium further comprises a saline solution.

17. An apparatus according to claim 10 wherein said internal cavity is the human gut.

18. An apparatus according to claim 10 wherein said internal cavity is the cranium.

19. A tonometric catheter apparatus for measuring at least one liquid fluid or gaseous fluid property indicative of the condition of an internal organ of a human or other mammal in vivo, comprising:
    (a) an elongated tonometric catheter tube comprising a first lumen and a second lumen extending longitudinally therethrough;
    (b) at least one walled sampling chamber on said catheter tube in fluid communication with the interior of said first lumen, said walled sampling chamber generally surrounding a portion of said catheter tube and being sealingly interconnected therewith., at least a portion of the wall of said sampling chamber being composed of a wall material that is freely and selectively permeable to one or more liquid fluids or gaseous fluids of interest, said wall material being substantially impermeable to other interfering liquid fluids or gaseous fluids, and said sampling chamber forming an interior space with said catheter tube in order to allow said one or more liquid fluids or gaseous fluids of interest from the tissue of the wall portion of the internal organ to permeate into said sampling chamber with a sampling medium, with said catheter tube extending to a position outside of the body of the human or other mammal;

(c) first sensor means for sensing the level of at least one of said liquid fluids or gaseous fluids of interest permeated from the tissue of the wall portion of the internal organ with said fluid sampling medium in sampling chamber;

(d) at least one walled pressure transmitting chamber on said catheter tube in pressure transmitting communication with the interior of said second lumen, said pressure transmitting chamber generally surrounding a portion of said catheter tube and being sealingly interconnected therewith, the wall of said pressure transmitting chamber being composed of a wall material that is substantially impermeable to liquid fluids or gaseous fluids normally encountered in vivo;

(e) a pressure transmitting medium within said pressure transmitting chamber for transmitting pressure received by said walled pressure transmitting chamber to said second lumen; and (f) pressure sensor means for sensing the pressure of said pressure transmitting medium.

20. The apparatus according to claim 19, wherein said sensor means further comprises a manometer located external to said human or other mammal.

21. The apparatus according to claim 19, wherein said pressure sensor means further comprises a pressure transducer located external to said human or other mammal.

22. The apparatus according to claim 21 wherein said pressure transmitting chamber and said sampling chamber share a common wall.

23. The apparatus of claim 22 wherein said common wall creates a single chamber for both pressure transmitting and fluid sampling.

24. An apparatus according to claim 19 wherein the wall material is silicone.

25. A tonometric catheter apparatus for measuring the internal pressure of a human or other mammal comprising:

(a) an elongated tonometric catheter tube having at least one lumen extending longitudinally therethrough;

(b) at least one walled pressure transmitting chamber in pressure transmitting communication with the interior of said lumen, so as to allow the transmission of change in said internal pressure through said pressure transmitting chamber to the interior of said lumen via a pressure transmitting medium, and wherein at least a portion of the wall of said chamber is composed of a wall material that is freely and selectively permeable to one or more liquid fluids or gaseous fluids of interest, said wall material being substantially impermeable to other interfering liquid fluids or gaseous fluids; and (c) pressure sensor means for measuring the pressure of said pressure transmitting medium.

26. An apparatus according to claim 25 wherein said wall of said pressure transmitting chamber is defined by a balloon member in sealing contact with a portion of said catheter.

27. An apparatus according to claim 25 wherein the wall of the chamber is composed of silicone.

28. A tonometric catheter apparatus for measuring at least one liquid fluid or gaseous fluid property indicative of either the internal pressure or the pH of an internal organ of a human or mammal in vivo comprising:

(a) an elongated tonometric catheter tube comprising lumen means extending longitudinally therethrough;

(b) a walled pressure transmitting sampling chamber on said catheter tube in fluid communication with the interior of said lumen means, said walled sampling pressure transmitting chamber generally surrounding a portion of said catheter tube and being sealingly interconnected therewith, said sampling chamber forming an interior space with said catheter tube in order to allow one or more liquid fluids or gaseous fluids of interest from the tissue of the walled portion of the internal organ to permeate into said pressure transmitting sampling chamber;

(c) a first sensor means for sensing the level of at least one of said liquid fluids or gaseous fluids of interest permeated from a tissue of the wall portion of the internal organ with a sampling medium;

(d) second sensor means for sensing the pressure of said sampling medium in said pressure transmitting sampling chamber.

29. The apparatus according to claim 28 wherein said second sensor means further comprises a pressure transducer for sensing the pressure of said sampling medium within said lumen means.

30. The apparatus according to claim 29 wherein said first sensor means is located in vivo and transmits a signal external to said human or other mammal via said lumen means.

31. An apparatus according to claim 30 wherein said sampling fluid comprises a saline solution.

32. An apparatus according to claim 28 wherein the wall material is silicone.

33. A method of monitoring the internal pressure of a human or other mammal comprising:

(a) inserting an elongated tonometric catheter tube having at least one lumen extending longitudinally therethrough into an organ of said human or other mammal;

said catheter having at least one walled pressure transmitting chamber in transmitting communication with the interior of said lumen, said walled chamber surrounding a portion of said catheter tube and being sealingly interconnected therewith, said pressure transmitting chamber forming an interior space with said catheter tube in order to allow the transmission of change in pressure through said pressure transmitting chamber to the interior of said lumen via a pressure transmitting medium;

(c) receiving a pressure indicating signal through said lumen;

(d) providing pressure sensor means for receiving said pressure indicating signal and converting it into a human readable form.

34. The method according to claim 33 wherein said receiving step further comprises receiving pressure transmitting medium on a pressure transducer.

35. The method according to claim 33 further comprising insufflating said pressure transmitting chamber with pressure transmitting medium after insertion in said human or other mammal; reading changes in said internal pressure over a period of time by repeatedly sensing the changes in the pressure transmitting medium pressure without removal or reinsertion of said catheter.

36. A method of monitoring the internal pressure of a human or other mammal and at least one liquid fluid or gaseous fluid property indicative of the pH of an internal organ of a human or mammal, in vivo, comprising the steps of:
  (a) inserting an elongated tonometric catheter tube having at least one lumen extending longitudinally therethrough into said human or other mammal;
  said catheter having at least one walled pressure transmitting and sampling chamber in fluid communication with the interior of said lumen, said walled pressure transmitting and sampling chamber generally surrounding a portion of said catheter tube and being sealingly interconnected therewith, said pressure transmitting and sampling chamber forming an interior space with said catheter tube in order to allow one or more liquid fluids or gaseous fluids of interest from the tissue of the walled portion of the internal organ to permeate into said pressure transmitting and sampling chamber and to allow the transmission of change in pressure through said pressure transmitting and sampling chamber to the interior of said lumen via a pressure transmitting medium;
  (b) providing a first sensor means for sensing the level of at least one of said liquid fluids or gaseous fluids of interest permeated from a tissue of the wall portion of the internal organ with a sampling medium;
  (c) receiving a pressure indicating signal through said lumen; and
  (d) providing a second sensor means for receiving said pressure indicating signal and converting it into a human readable form.

37. The method according to claim 36 further comprising insufflating said pressure transmitting and sampling chamber with pressure transmitting medium after insertion in said human or other mammal; reading changes in said internal pressure over a period of time by repeatedly sensing the changes in the pressure transmitting medium pressure without removal or reinsertion of said catheter.

38. A method according to claim 36 wherein the wall of the chamber is composed of silicone.

39. An apparatus according to claim 10 wherein the wall material is silicone.

* * * * *